(12) United States Patent
Hoffman

(10) Patent No.: US 11,999,518 B2
(45) Date of Patent: Jun. 4, 2024

(54) PHARMACEUTICAL ORDER PROCESSING SYSTEMS AND METHODS

(71) Applicant: Express Scripts Strategic Development, Inc., St. Louis, MO (US)

(72) Inventor: Robert E. Hoffman, Linden, IN (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 349 days.

(21) Appl. No.: 17/551,776

(22) Filed: Dec. 15, 2021

(65) Prior Publication Data

US 2022/0185510 A1 Jun. 16, 2022

Related U.S. Application Data

(60) Provisional application No. 63/125,485, filed on Dec. 15, 2020.

(51) Int. Cl.
*B65B 3/00* (2006.01)
*B65C 9/02* (2006.01)
(Continued)

(52) U.S. Cl.
CPC .............. *B65B 3/003* (2013.01); *B65C 9/02* (2013.01); *G16H 20/10* (2018.01); *G16H 40/20* (2018.01); *B65G 1/04* (2013.01); *B65G 59/10* (2013.01)

(58) Field of Classification Search
CPC .... B65G 1/0464; B65G 1/1373; B65G 59/02; B65G 1/137; B65G 59/10; B65G 1/04;
(Continued)

(56) References Cited

U.S. PATENT DOCUMENTS 5,208,762 A * 5/1993 Charhut ................ A61J 7/0084
221/9
5,771,657 A * 6/1998 Lasher .................... B65B 61/20
53/493

(Continued)

FOREIGN PATENT DOCUMENTS

CA 2555327 C * 2/2016 ............. G06Q 50/22
EP 1388336 A1 * 2/2004 ............. B65B 5/103

OTHER PUBLICATIONS

Schultz, et al., Pharmaceutical Container Holder, U.S. Appl. No. 17/093,831, filed Nov. 10, 2020, The present application and U.S. Appl. No. 17/039,831 are commonly assigned to Express Scripts Strategic Development, Inc.

*Primary Examiner* — James R Bidwell
(74) *Attorney, Agent, or Firm* — Stinson LLP

(57) ABSTRACT

A pharmaceutical container processor for processing pharmaceutical containers includes a set of container operation stations along which a set of container operations occur. The set of container operation stations includes a storage station where pharmaceutical containers are stored; a first identification station where pharmaceutical containers are each identified; a labeling station where a label is applied to pharmaceutical containers; a second identification station where pharmaceutical containers are each identified after the label is applied; and an outlet station where pharmaceutical containers are moved to after said pharmaceutical containers are identified at the second identification station. First and second container transporters move each pharmaceutical container through the set of container operation stations. Each pharmaceutical container is transferred from the first container transporter to the second container transporter along the set of container operation stations.

20 Claims, 18 Drawing Sheets

(51) Int. Cl.
 *B65G 1/04* (2006.01)
 *B65G 59/10* (2006.01)
 *G16H 20/10* (2018.01)
 *G16H 40/20* (2018.01)

(58) Field of Classification Search
 CPC ........... B65G 47/91; B65B 3/003; B65C 9/02; G16H 40/20; G16H 20/10
 See application file for complete search history.

(56) References Cited

U.S. PATENT DOCUMENTS

| | | |
|---|---|---|
| 7,412,814 B2 | 8/2008 | Rice |
| 7,506,472 B2 | 3/2009 | Leyns |
| 8,892,245 B2 | 11/2014 | Joplin |
| 9,242,751 B1 | 1/2016 | Joplin |
| 9,373,065 B1 | 6/2016 | Hoffman |
| 9,457,926 B2 | 10/2016 | Schach |
| 9,561,876 B2 | 2/2017 | Ehmer |
| 9,665,688 B2 | 5/2017 | Terzini |
| 9,697,335 B2 | 7/2017 | Joplin |
| 9,937,100 B1 | 4/2018 | Joplin |
| 9,944,419 B2 | 4/2018 | Joplin |
| 9,978,036 B1 | 5/2018 | Eller |
| 10,053,248 B2 | 8/2018 | Joplin |
| 10,196,253 B2 | 2/2019 | Clüsserath |
| 10,433,477 B2 | 10/2019 | Sheppard |
| 10,661,993 B2 | 5/2020 | Joplin |
| 10,669,098 B1* | 6/2020 | Terzini ................... G16H 40/20 |
| 11,226,348 B2* | 1/2022 | Vollenweider ......... G01N 35/04 |
| 11,820,543 B1* | 11/2023 | Hoffman .................... B65B 5/06 |
| 2005/0171813 A1* | 8/2005 | Jordan ................ G07F 17/0092 700/231 |
| 2014/0137521 A1 | 5/2014 | Niehr |
| 2014/0266716 A1 | 9/2014 | Boissonneault |
| 2018/0210000 A1 | 7/2018 | Van Mierlo |

\* cited by examiner

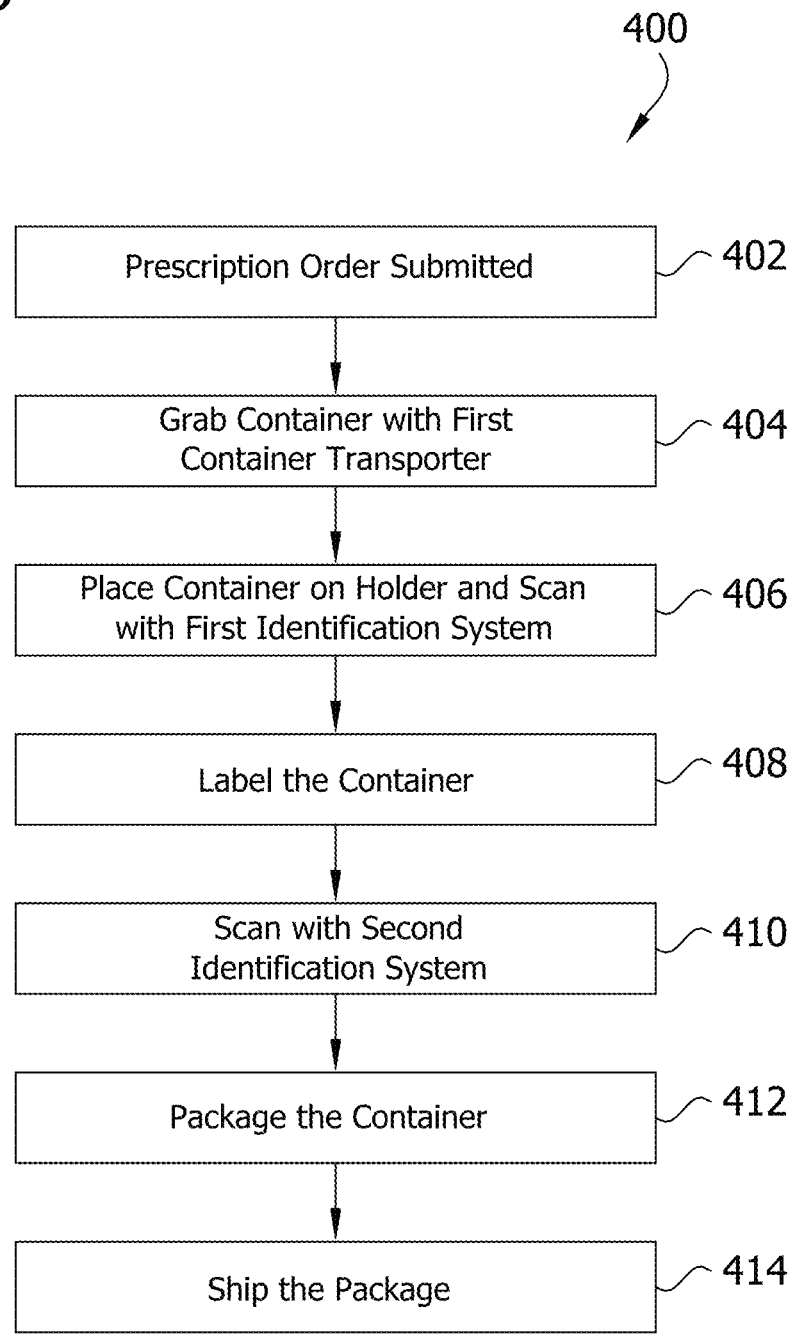

PHARMACEUTICAL ORDER PROCESSING SYSTEMS AND METHODS

CROSS REFERENCE TO RELATED APPLICATIONS

This application claims priority to U.S. Provisional Patent Application No. 63/125,485, entitled "PHARMACEUTICAL ORDER PROCESSING SYSTEMS AND METHODS" and filed on Dec. 15, 2020, and this application is incorporated herein by reference.

FIELD

The present disclosure generally relates to pharmaceutical order processing systems, and more particularly to pharmaceutical container processing systems for processing pharmaceutical containers.

BACKGROUND

High volume pharmacies process and fulfill a large number of prescription orders per day. These pharmacies often rely on automated systems to process, fill, and pack one or more prescriptions together for delivery to a patient. These automated systems generally fit into one of two categories: (1) systems, such as high-volume fillers, that automatically fill pharmaceutical containers (e.g., auto-filled containers) with specific quantities of pharmaceuticals; and (2) systems, such as unit-of-use systems, that process unit-of-use products or containers. A unit-of-use container contains an entire prescription of a pharmaceutical and can therefore be sent to the patient without modifying the pharmaceutical(s) (e.g., the quantity, type, etc.) in the container and without product packaging modification (or with minimal product packaging modification) except for labeling with patient information. Unit-of-use products can include a full course of medicine to be taken by a patient, for example, an entire prescription (e.g., a thirty-day supply, a sixty-day supply, or a ninety-day supply). The unit-of-use products contain known quantities of medication in packages that are closed and sealed by, for example, the pharmaceutical manufacturer.

SUMMARY

In one aspect, a pharmaceutical container processor for processing pharmaceutical containers comprises a set of container operation stations along which a set of container operations occur. The set of container operation stations includes a storage station, a first identification station, a labeling station, a second identification station and an outlet station. The pharmaceutical containers are stored at the storage station. The pharmaceutical containers are each identified at the first identification station after being removed from the storage station. The label is applied to pharmaceutical containers at the labeling station after pharmaceutical containers are identified at the first identification station. The pharmaceutical containers are each identified at the second identification station after the label is applied to said pharmaceutical containers. The pharmaceutical containers are then moved to the outlet station after said pharmaceutical containers are identified at the second identification station. First and second container transporters are configured to move each pharmaceutical container through the set of container operation stations. Each pharmaceutical container is transferred from the first container transporter to the second container transporter along the set of container operation stations.

Other objects and features of the present disclosure will be in part apparent and in part pointed out herein.

BRIEF DESCRIPTION OF THE DRAWINGS

FIG. 18 is an example flow diagram of the operation of the pharmaceutical container processing system according to one embodiment of the present disclosure.

Corresponding reference characters indicate corresponding parts throughout the drawings.

DETAILED DESCRIPTION

Figure 1:
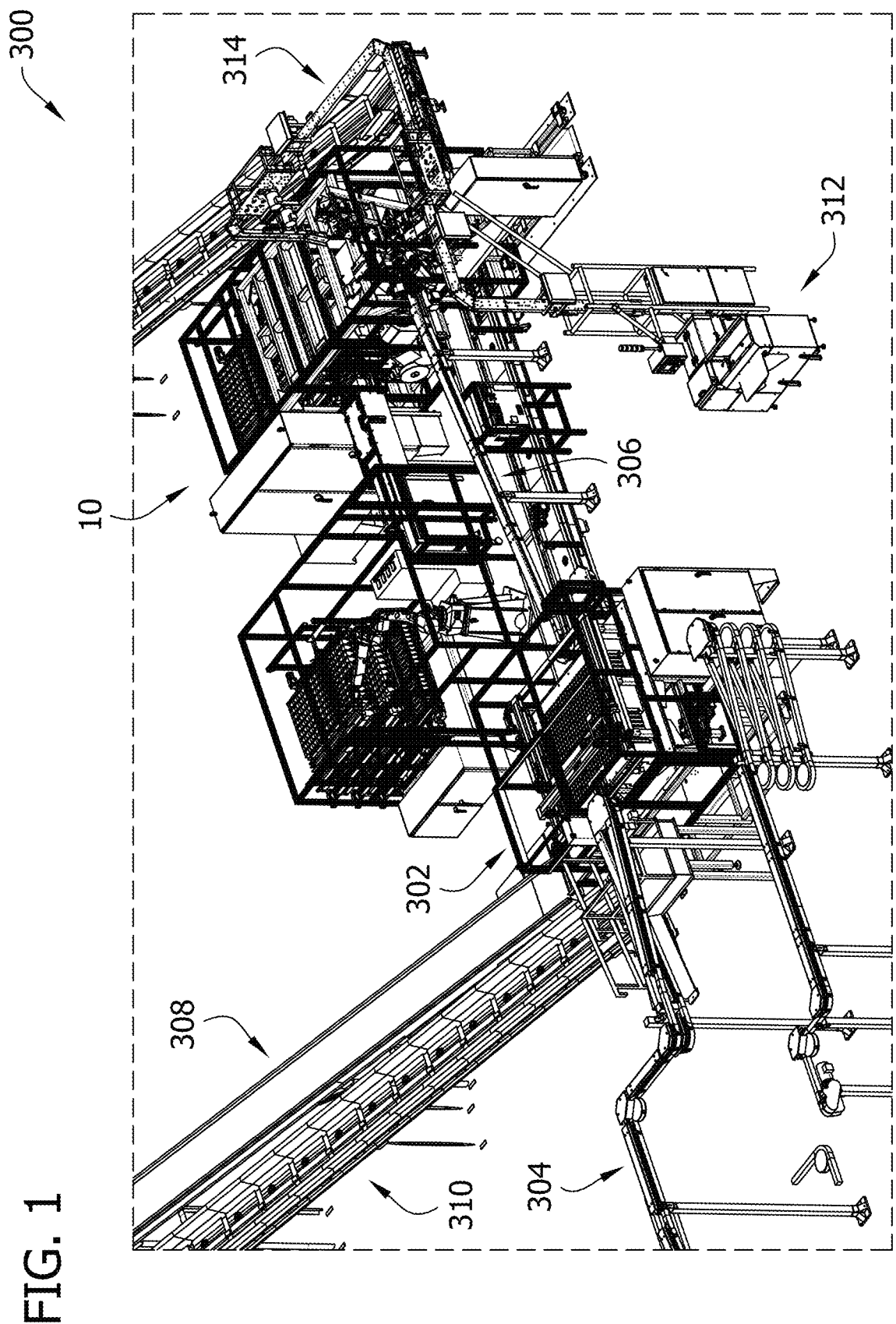
FIG. 1 is a perspective of a pharmaceutical order processing system according to one embodiment of the present disclosure.
Figure 2:
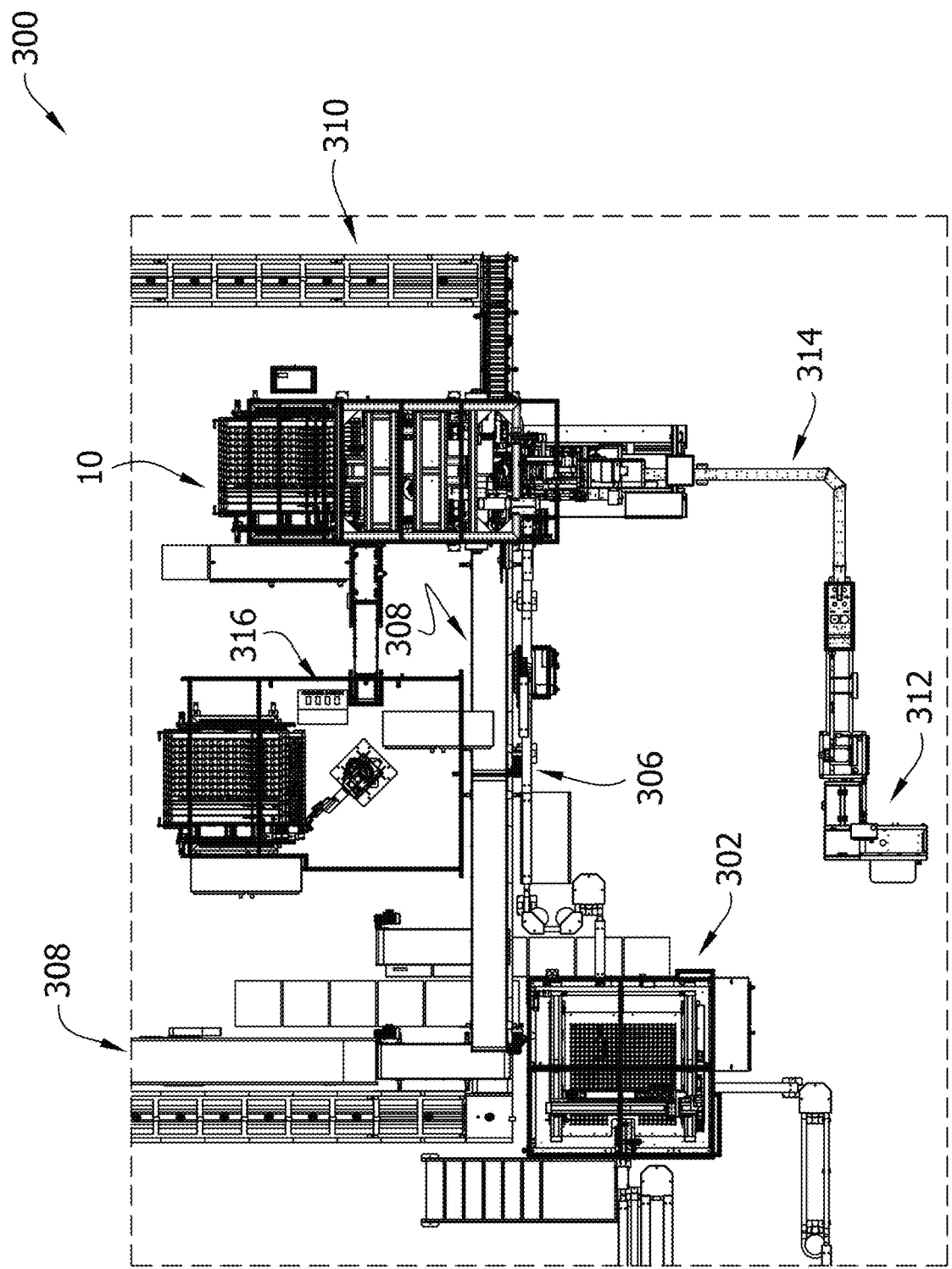
FIG. 2 is a plan view of the pharmaceutical order processing system.

Referring to FIGS. 1 and 2, a pharmaceutical order processing system according to one embodiment of the present disclosure is indicated generally by reference numeral 300. The pharmaceutical order processing system 300 processes prescription orders received by the system. A prescription order may include one or more pharmaceuticals (e.g., prescription drugs), which are contained in pharmaceutical containers C. The pharmaceutical containers C may be in the form of a bottle, a box, or any other suitable container. In this embodiment, the pharmaceutical order processing system 300 is a mix system comprising both unit-of-use container systems that process pharmaceutical containers C that are generally unit-of-use products and high-volume pharmaceutical order processing system (e.g., a high-volume filler) that fills empty pharmaceutical containers C with specific quantities of pharmaceuticals. In the illustrated embodiment, the pharmaceutical order processing system 300 includes a pharmaceutical container processing system 10 (described in more detail below) for processing unit-of-use products, a high-volume filler (not shown), a bottle table 302 (broadly, an order consolidation station or order staging station) for staging pharmaceutical containers C from the high-volume filler, and corresponding conveyors (e.g., conveyor belts) for conveying or moving items (e.g., pharmaceutical containers, packages, bins 106) about the pharmaceutical order processing system.

The pharmaceutical order processing system 300 includes a first or high-volume filler conveyor 304 that generally transports pharmaceutical containers C (e.g., bottles) from the high-volume filler to the bottle table 302. The bottle table 302 is configured to stage the pharmaceutical containers C from the high-volume filler. The bottle table 302 may group two or more pharmaceutical containers C that are part of the same order together. The bottle table 302 may then release the pharmaceutical containers C toward the pharmaceutical container processing system 10 to be packaged with the unit-of-use products or package the pharmaceutical containers themselves. For example, the bottle table 302 may release pharmaceutical containers C toward the pharmaceutical container processing system 10 when the pharmaceutical containers held by the bottle table 302 are part of prescription order comprising unit-of-use products (e.g., unit-of-use pharmaceutical containers from the pharmaceutical container processing system). This allows to the pharmaceutical order processing system 300 to combine pharmaceutical containers C from difference sources (e.g., the pharmaceutical container processing system 10 and the high-volume filler) that make up a prescription order into the same packaging for shipping to the patient. The pharmaceutical order processing system 300 includes a second or bottle table conveyor 306 that generally transports the pharmaceutical containers C from the bottle table 302 to the pharmaceutical container processing system 10. Further details on the bottle table 302 may be found in U.S. Pat. Nos. 7,412,814 and 9,242,751, the entireties of which are incorporated herein by reference. The illustrated pharmaceutical order processing system 300 also includes a third or package conveyor 308 for transporting packages (e.g., shipping bags) away from the pharmaceutical container processing system 10 to another location, such as a shipping station. The pharmaceutical order processing system 300 also includes a fourth or bin conveyor 310 for transporting collection bins 106 toward, through and away from the pharmaceutical container processing system 10. The bin conveyor 310 may transport bins 106 (e.g., empty bins) to the pharmaceutical container processing system 10 to receive processed pharmaceutical containers C (e.g., a shipping package containing one or more pharmaceutical containers) and for transporting the bin (and items contained therein) to another location, such as the shipping station.

The illustrated pharmaceutical order processing system 300 also includes a literature distribution unit or literature processor 312 configured to supply the literature corresponding to the prescription order for packaging with the pharmaceuticals containers C processed by the pharmaceutical container processing system 10. The pharmaceutical order processing system 300 includes a fifth or literature conveyor 314 which generally transports the literature from the literature processor 312 to the pharmaceutical container processing system 10 (e.g., a bagger). Further details on pharmaceutical order processing systems and components thereof, including unit-of-use systems and high-volume fillers, may be found in U.S. Pat. Nos. 9,373,065, 9,697,335, 9,944,419, 9,978,036, and 10,053,248, the entities of which are hereby incorporated by reference. However, it will be appreciated that the systems and components disclosed herein can be used in other contexts without departing from the scope of the present disclosure.

Figure 3:
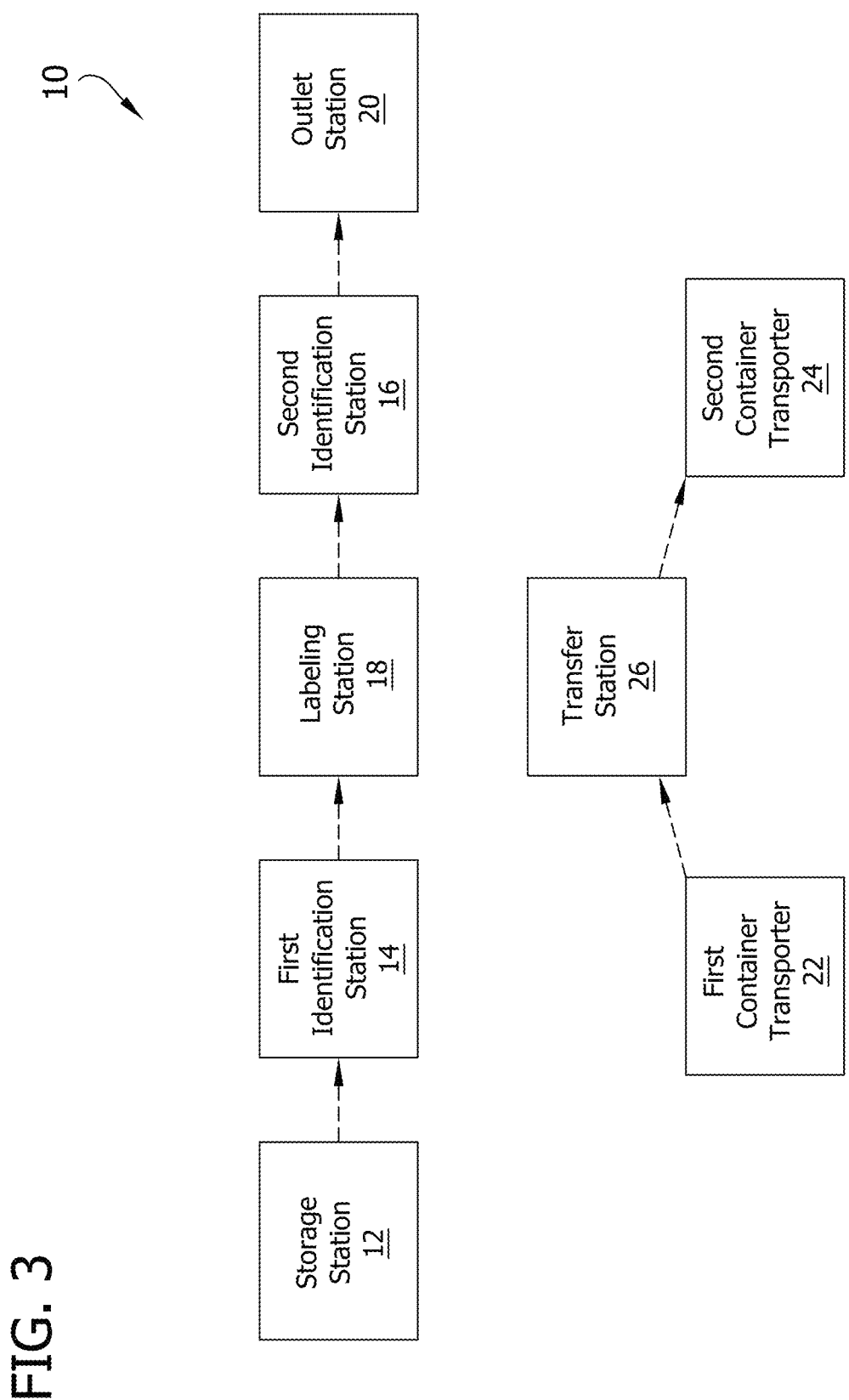
FIG. 3 is a schematic of a pharmaceutical container processing system according to one embodiment of the present disclosure.

Referring to FIG. 3, a pharmaceutical container processing system (e.g., pharmaceutical container processor) according to one embodiment of the present disclosure is indicated generally by reference numeral 10. The pharmaceutical container processing system 10 is shown schematically in FIG. 3. The pharmaceutical container processing system 10 may be the pharmaceutical container processing system that is part of the pharmaceutical order processing system 300 of FIGS. 1 and 2, or may be a standalone system. The pharmaceutical container processing system 10 processes prescription orders received by the system. Specifically, the pharmaceutical container processing system 10 may process a select category or subset of prescription orders received by the pharmaceutical order processing system 300, such as prescription orders comprising unit-of-use products. Accordingly, the pharmaceutical container processing system 10 comprises a unit-of-use system that processes pharmaceutical containers C that are unit-of-use products. The pharmaceutical container processing system 10 generally stores, monitors, labels, dispenses and packages the unit-of-use pharmaceutical containers C. As mentioned above, the pharmaceutical container processing system 10 may also be used with non-unit-of-use systems, such as a high-volume pharmaceutical order processing system (e.g., a high-volume filler).

The pharmaceutical container processing system 10 (e.g., system) processes the pharmaceutical containers C (e.g., a plurality of pharmaceutical containers) to fill prescription orders. To process the plurality of pharmaceutical containers C, the system 10 includes a set of container operation stations (described in more detail below) along which a set of container operations occur. Broadly, a station is where one or more operations (e.g., functions) occur to further the processing of the pharmaceutical containers C to fill a prescription order and may include the one or more components that perform the one or more operations (i.e., the one or more components are at the station). The set of container operations may include one or more of storing, monitoring, labeling, dispensing, transporting, verifying, and/or packaging the pharmaceutical container C. Other container operations are also within the scope of the present disclosure. In addition, more than one container operation may occur at a container station. Desirably, the system 10 includes a storage station 12, one or more identification stations (e.g., a first identification station 14, a second identification station 16, etc.), a labeling station 18, an outlet station 20, two or more container transporters (e.g., a first container transporter 22, a second container transporter 24, etc.), and/or a transfer station 26. The system 10 may include more or less of each station as well as include stations other than described herein. Generally, the storage station 12, the one or more identification stations (e.g., the first identification station 14, the second identification station 16, etc.), the labeling station 18, the outlet station 20, the two or more container transporters (e.g., the first container transporter 22, the second container transporter 24, etc.), and/or the transfer station 26 are used to process the unit-of-use pharmaceutical containers C by storing, monitoring, labeling, dispensing, transporting, verifying and/or packaging the pharmaceutical containers to fill a prescription order received by the system 10. Accordingly, the system 10 is an automated system use to auto-fill or auto-process received prescription orders. The general movement of the pharmaceutical containers between these different stations is generally indicated by the dash arrows in FIG. 3, although other paths of movements between the stations are within the scope of the present disclosure.

In general, the storage station 12 is where the plurality of pharmaceutical containers C are stored. The first identification station 14 is where the plurality of pharmaceutical containers C are each identified after being removed from the storage station 12. The labeling station 18 is where a label (e.g., a patient specific label) is applied to the plurality of pharmaceutical containers C after the containers are identified at the first identification station 14. The second identification station 16 is where the plurality of pharmaceutical containers C are each identified after the label is applied to the containers at the labeling station 18. The outlet station 20 is where the plurality of pharmaceutical containers C are moved to after the containers are identified at the second identification station 16 for further processing such as packaging or marrying with other containers. The first container transporter 22 and the second container transporter 24 are configured to move each container C through the operation stations. Generally, each pharmaceutical container C is moved, in order, through the storage station 12, the first identification station 14, the labeling station 18, the second identification station 16 and then the outlet station 20. At some point along the set of operation stations, each container C is transferred from the first container transporter 22 to the second container transporter 24. The transfer between the first container transporter 22 to the second container transporter 24 occurs at the transfer station 26. The transfer station 26 can be arranged generally anywhere between the storage station 12 and the outlet station 20. By using two container transporters 22, 24 to move a container along the operation stations (e.g., the storage station 12, the one or more identification stations 14, 16, the labeling station 18, the outlet station 20, and the transfer station 26), the system 10 can process pharmaceutical containers C faster than conventional systems. For example, conventional systems that only use one container transporter can typically process a container C in about 10-11 seconds, whereas a system 10 of the present disclosure can process a container in about 5-6 seconds. Accordingly, the system 10 of the present disclosure is about twice as fast as conventional systems and can therefore process about twice as many containers C over a conventional system in a given time frame.

Referring to FIGS. 4-14 and 16, another embodiment of a pharmaceutical container processing system is generally shown. The pharmaceutical container processing system shown in FIGS. 4-14 and 16 is analogous to the pharmaceutical container processing system 10 shown in FIG. 3. Accordingly, for ease of comprehension, the pharmaceutical container processing system shown in FIGS. 4-14 and 16 includes identical reference numerals to that of the pharmaceutical container processing system 10 shown in FIG. 3 where the system of FIGS. 4-14 and 16 contains similar, analogous or identical parts to that of the system of FIG. 3. Similarly, it is understood that the system 10 of FIG. 3 may include one or more of the components of the system of FIGS. 4-14 and 16. In this embodiment, the pharmaceutical container processing system 10 shown in FIGS. 4-14 and 16 is the pharmaceutical container processing system that is part of the pharmaceutical order processing system 300 of FIGS. 1 and 2 (and shown in FIGS. 1 and 2).

The pharmaceutical container processing system 10 ("system") of FIGS. 4-14 and 16 includes a storage station 12, a first identification station 14, a second identification station 16, a labeling station 18, an outlet station 20, a first container transporter 22, a second container transporter 24, and a transfer station 26.

Figure 4:
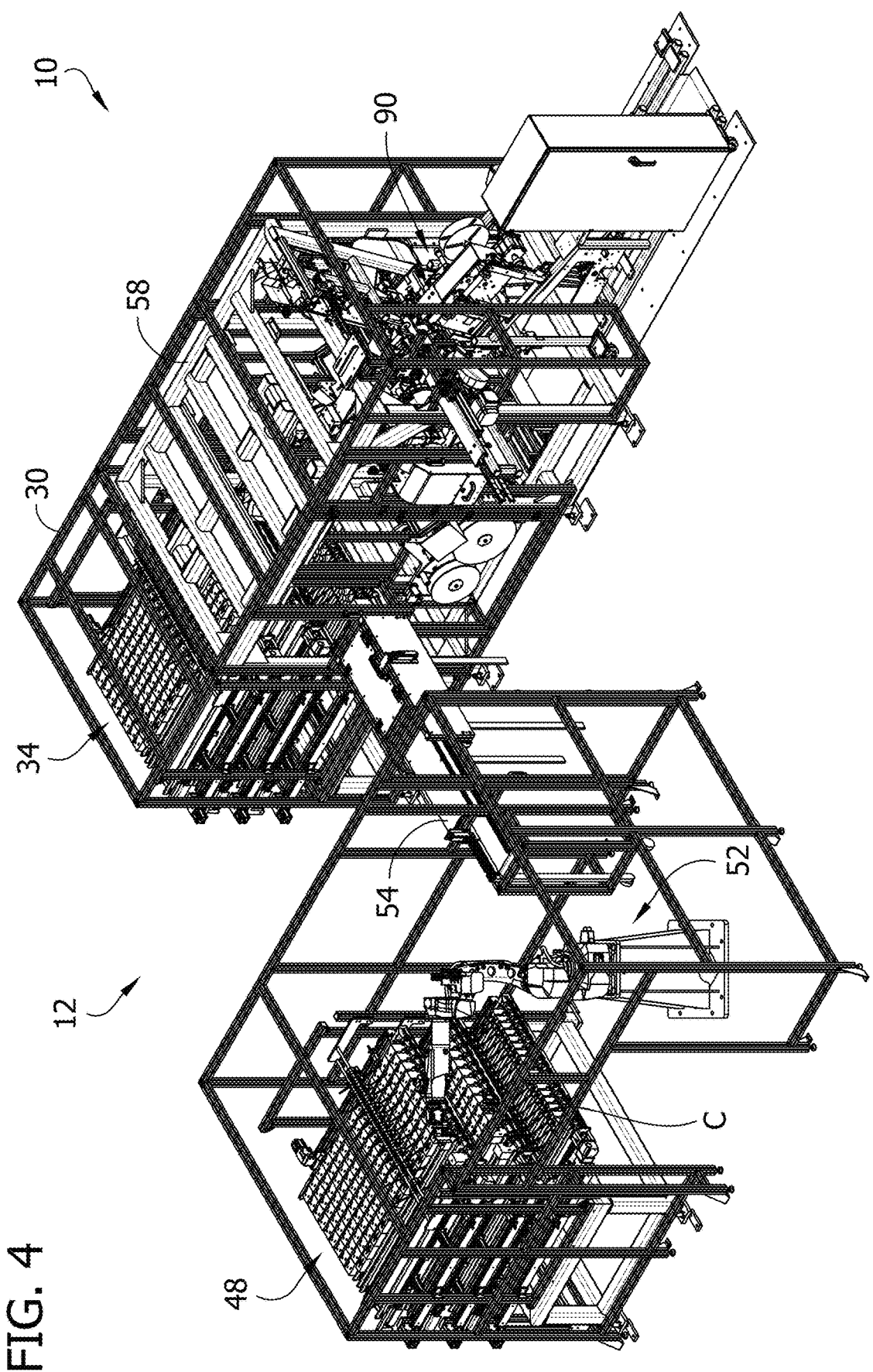
FIG. 4 is a perspective of a pharmaceutical container processing system according to another embodiment of the present disclosure.
Figure 6:
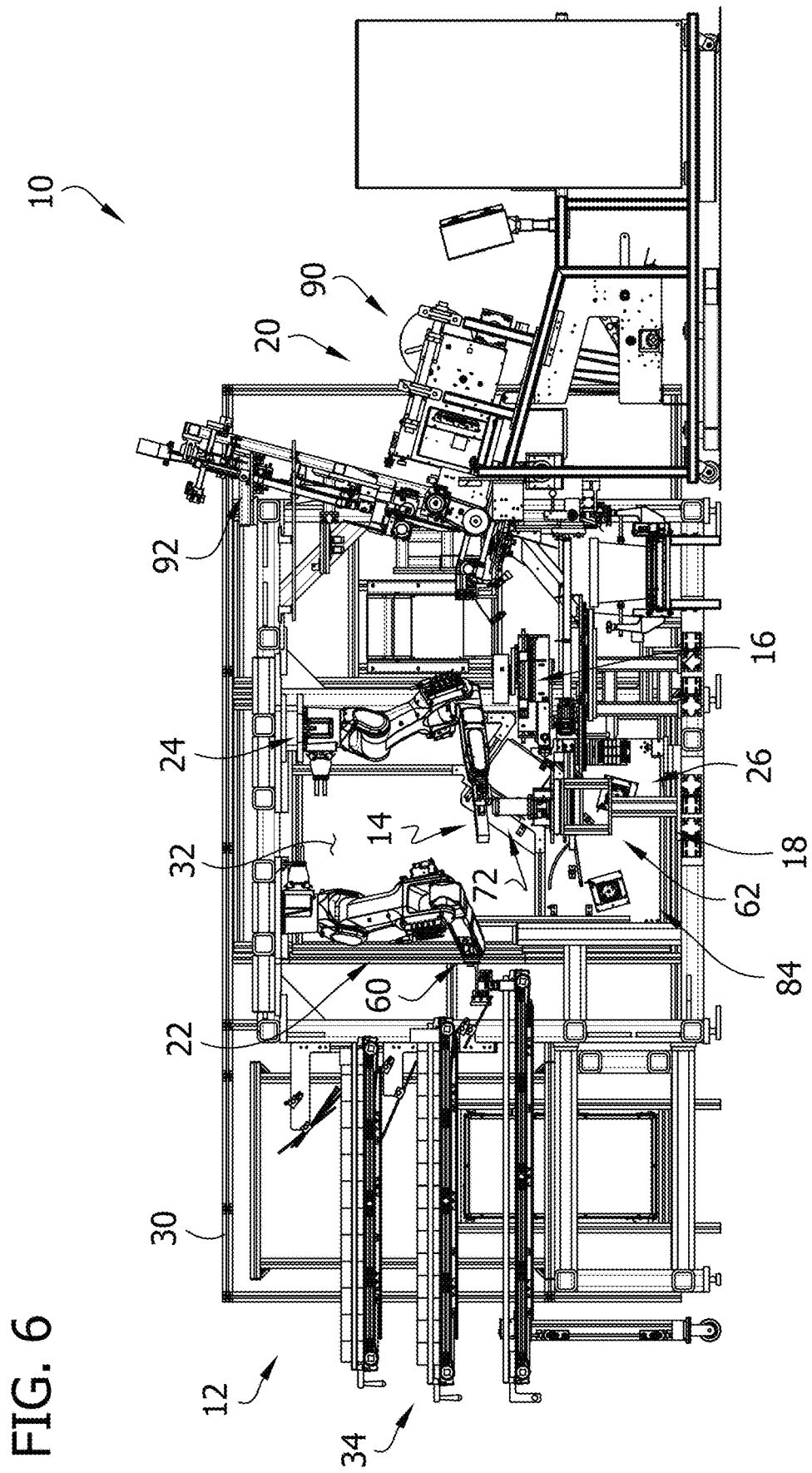
FIG. 6 is a cross-section of the pharmaceutical container processing system of FIG. 4 taken generally through a longitudinal center of the system.

Referring to FIGS. 4 and 6, the system 10 includes an enclosure 30. The enclosure 30 defines (e.g., encloses) a processing area 32. The set of container stations are generally disposed in the processing area 32 such that the series of container operations takes place within the processing area (e.g., enclosure 30). The storage station 12, the first identification station 14, the labeling station 18, the second identification station 16, the transfer station 26 and the outlet station 20 are at least partially disposed in the processing area 32. In the illustrated embodiment, the first identification station 14, the labeling station 18, the second identification station 16, and the transfer station 26 are disposed entirely within the processing area 32 and the storage station 12 and the outlet station 20 are partially disposed in the processing area. The enclosure 30 helps keep the processing area 32 and components therein clean.

Referring to FIGS. 4-8, the system 10 includes a first container repository 34 (broadly, at least one container repository) at the storage station 12. The first repository 34 is configured to hold and store pharmaceutical containers C. The first repository 34 receives and holds the pharmaceutical containers C and can hold many different types of pharmaceutical containers (e.g., types of pharmaceuticals). The first repository 34 can be configured to hold pharmaceutical containers C of different shapes and of generally any size. For example, the first repository 34 can configured for bottles, boxes and other shapes and any combination thereof. In one embodiment, the pharmaceutical containers C are manually loaded onto (e.g., into) the first repository 34 by an operator. The enclosure 30 can define an opening to permit the containers C to be manually loaded by the operator.

In the illustrated embodiment, the first repository 34 includes a plurality (broadly, at least one) of shelves or racks 36 configured to support (e.g., hold) the pharmaceutical containers C. In the illustrated embodiment, the first repository 34 includes three racks 36, although more or fewer racks are within the scope of the present disclosure. Each rack 36 may support many different types, shapes, sizes, etc. of pharmaceutical containers C. In the illustrated embodiment, the racks 36 are supporting bottle-shaped containers C. The racks 36 are generally identical. Each rack 32 includes a plurality of channels 38 sized and shaped so that the pharmaceutical containers C are arranged one after another (e.g., single file) in the channel. Desirably, the widths of the channels 38 are adjustable to configure the channels to different sizes of containers C. Opposite sides of the channels 38 are defined by guides 40 which are preferably movable relative to one another to adjust the size (e.g., width) of the channel to conform to the size (e.g., width) of the pharmaceutical containers C placed therein. For example, the guides 40 can move toward or away from one another to increase or decrease the width of the channel 38. The guides 40 may move conjointly in opposite directions. Preferably, the guides 40 are equally spaced from a centerline of the channel 38. In one embodiment, both the guides 40 move (e.g., move simultaneously) to change the size of the channel 38 and move in such a manner that they remain equally distant from a centerline of the channel. For example, both guides 40 move outward (e.g., away from one another) by the same distance to enlarge the size of the channel 38 and move inward (e.g., toward one another) by the same distance to reduce the size of the channel, to correspond to the dimensions of the container C. This keeps the centerline of the channel 38 in the same position, regardless of the size of the channel, which helps facilitate the removal of the pharmaceutical containers C from the first repository 34 by the first container transporter 22. Keeping the centerline of the channel 38 in the same position reduces the amount of calibrating that needs to be done with the first container transporter 22 when the size of the channel 38 is changed. Movement of the guides 40 may be performed manually. In operation, each channel 38 of the first repository 34 is filled with the same type of pharmaceutical containers C (e.g., all the pharmaceutical containers in the channel contain the same type and quantity of a pharmaceutical).

Each rack 36 includes a conveyor 42 that defines the platform supporting the containers C (e.g., defines the base of the channels 38). One or more prime movers 44 (e.g., an electric motor) is operatively coupled to the conveyor 42 for moving the conveyor and thereby the containers C there on within the channels 38. In the illustrate embodiment, each rack 36 includes on conveyor 42 for all the channels 38. The conveyor 42 moves the pharmaceutical containers C in the channel 38 toward a pick-up location located at the front of the first repository 34. Each pick-up location is generally at the forward end of each channel 38. The conveyor 42 moves the pharmaceutical containers C forward, toward (e.g., into) the pick-up location, where the first container transporter 22 grabs the pharmaceutical containers. Accordingly, as pharmaceutical containers C are removed from the pick-up locations of the first repository 34, the conveyor 42 moves subsequent pharmaceutical containers into the pick-up positions. Each rack 36 may include a container sensor 46 at each pick-up location. The container sensor 46 is configured to detect the presence of a pharmaceutical container C at the pick-up location. The container sensor 42 may comprise any suitable sensor for detecting the presence of a pharmaceutical container such as but not limited to a pressure sensitive switch or a proximity sensor (e.g., a photoelectric sensor). In one embodiment, the conveyors 42 may run continuously, only stopping when a pharmaceutical container C is being grabbed by the first container transporter 22. In this embodiment, the sensor 42 may simply be used to determine if the corresponding channel 38 contains pharmaceutical containers C or not. In another embodiment, the container sensors 46 and conveyors 42 operate as a closed-loop system, with the conveyor 40 operating (e.g., moving) automatically after the container sensor no longer detects the presence of a pharmaceutical container C and continuing to move until the container sensor detects the presence of a pharmaceutical container, at which point the conveyor stops.

Figure 16:
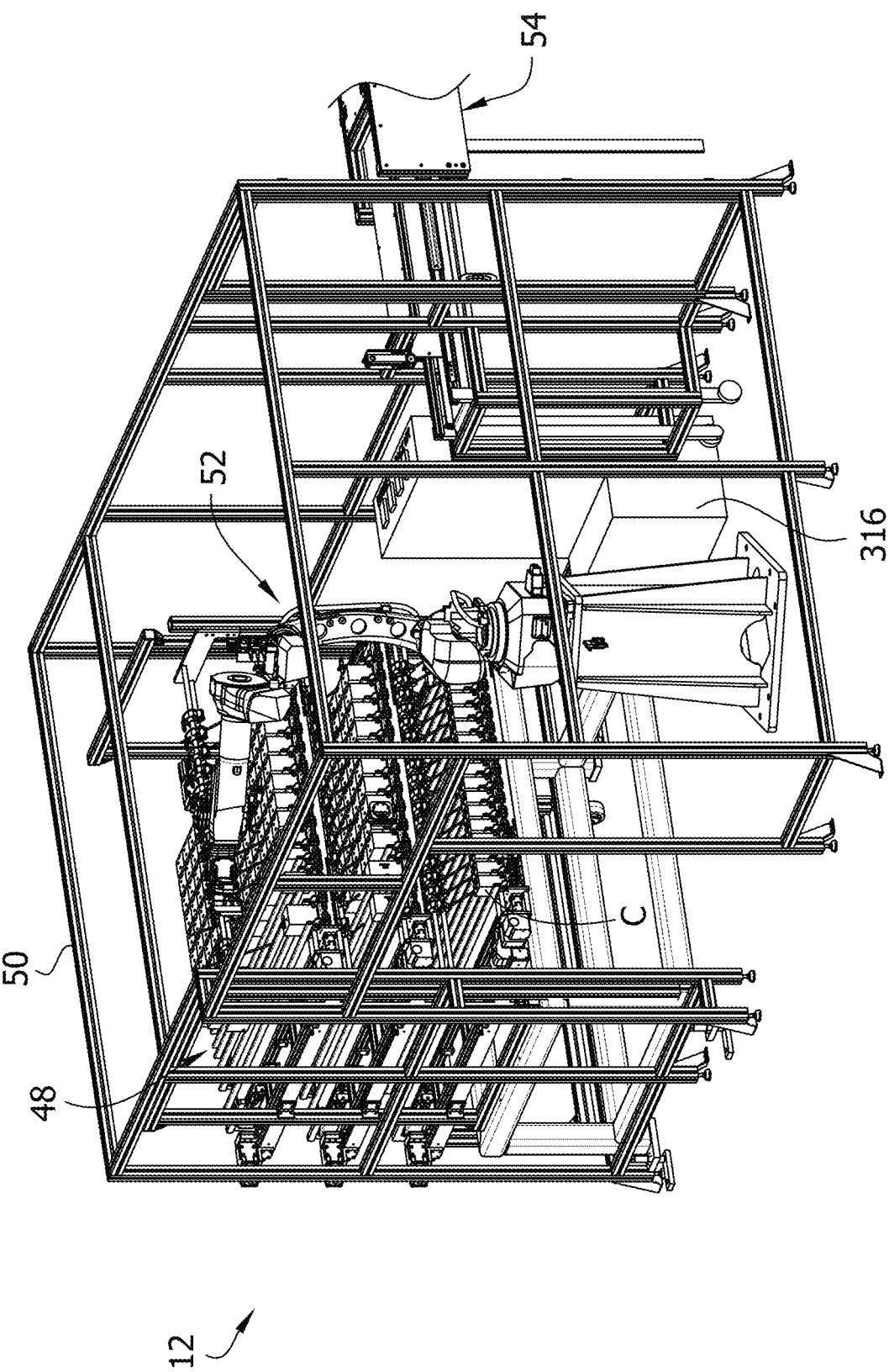
FIG. 16 is a perspective of a second repository of the pharmaceutical container processing system of FIG. 4.

Referring to FIGS. 4 and 16, in the illustrated embodiment, the system 10 includes a second container repository 48. The second repository 48 is identical to the first repository 34. The second repository 48 increases the capacity of the system 10—i.e., how many different types of containers C the system can process. In one method of operation, the first repository 34 may be set up to hold and store bottle-shaped containers C while the second repository 48 is set up to hold and store box-shaped containers. The second repository 48 is spaced apart from the processing area 32 and is surround by its own enclosure 50. To move the containers C from the second repository 48 to the processing area 32 and be grabbed by the first container transporter 22, the system 10 includes a second repository picker 52 and a second repository conveyor 54. In the illustrated embodiment, the second repository picker 52 comprises a robot such as a six-axis robotic arm, although other robots are within the scope of the present disclosure. For example, the second repository picker 52 may comprise a selective-compliance-articulated robotic arm, a cylindrical robot, a delta robot, a polar coordinate robot, a vertically articulated robot, a Cartesian coordinate robot or any other suitable device. The second repository picker 52 includes a gripper 56 configured to grip the container C. The gripper 56 may include movable jaws, a suction pad, a suction bag (e.g., a bag with suction inlets and filled with beads that conforms to the shape of the container C) or any other suitable mechanism for gripping the containers C. The second repository picker 52 removes the containers C from the second repository 48 and places the containers on the second repository conveyor 54. The second repository conveyor 54 generally extends from the second repository 48 to the processing area 32. The second repository conveyor 54 transports the containers C placed thereon into the processing area 32, where the first container transporter 22 can grab them (e.g., the end of the second repository conveyor 54 defines a pick-up location for the first container transporter 22 to grab the container from). In the illustrated embodiment, the second repository conveyor 54 is disposed in an enclosure extending between the two enclosures 30, 50 of the system 10. It is understood the system 10 can include additional container repositories and associated components (e.g., conveyors, pickers, etc.). For example, in the illustrated embodiment, the storage station 12 also includes a foil pack dispenser 316 (broadly, a third repository) for dispensing foil packs (another type of pharmaceutical container). In this embodiment, the foil pack dispenser 316 is in the same enclosure 50 as the second repository 48. The foil packs can be grabbed from the foil pack dispenser 316 and transported to processing area 32 in generally the same manner as the pharmaceutical containers from the second repository 48. Further details on the foil pack dispenser 316 may be found in U.S. patent application Ser. No. 17/093,831, filed on Nov. 10, 2020, the entirety of which is hereby incorporated by reference. It is understood the storage station 12 can be further expanded by placing additional container repositories around the second repository picker 52 and/or extending the repository conveyor 54 to add additional repository pickers and associated container repositories.

Other configurations of the repositories 34, 48 are within the scope of the present disclosure. For example, in one embodiment, a container repository (not shown) can hold and store boxes in a stacked arrangement. In this embodiment, a picker, such as the second repository picker 52, could remove the boxes from the stacked arrangement. The box may be removed from the stack by the picker and/or removed from the stack by a dispenser (not shown), such as a pusher. This container repository could be placed within the same enclosure 50 as the second repository 48. Accordingly, the second repository picker 52 and the second repository conveyor 54 could also move these stacked containers to the processing area 32.

Figure 5:
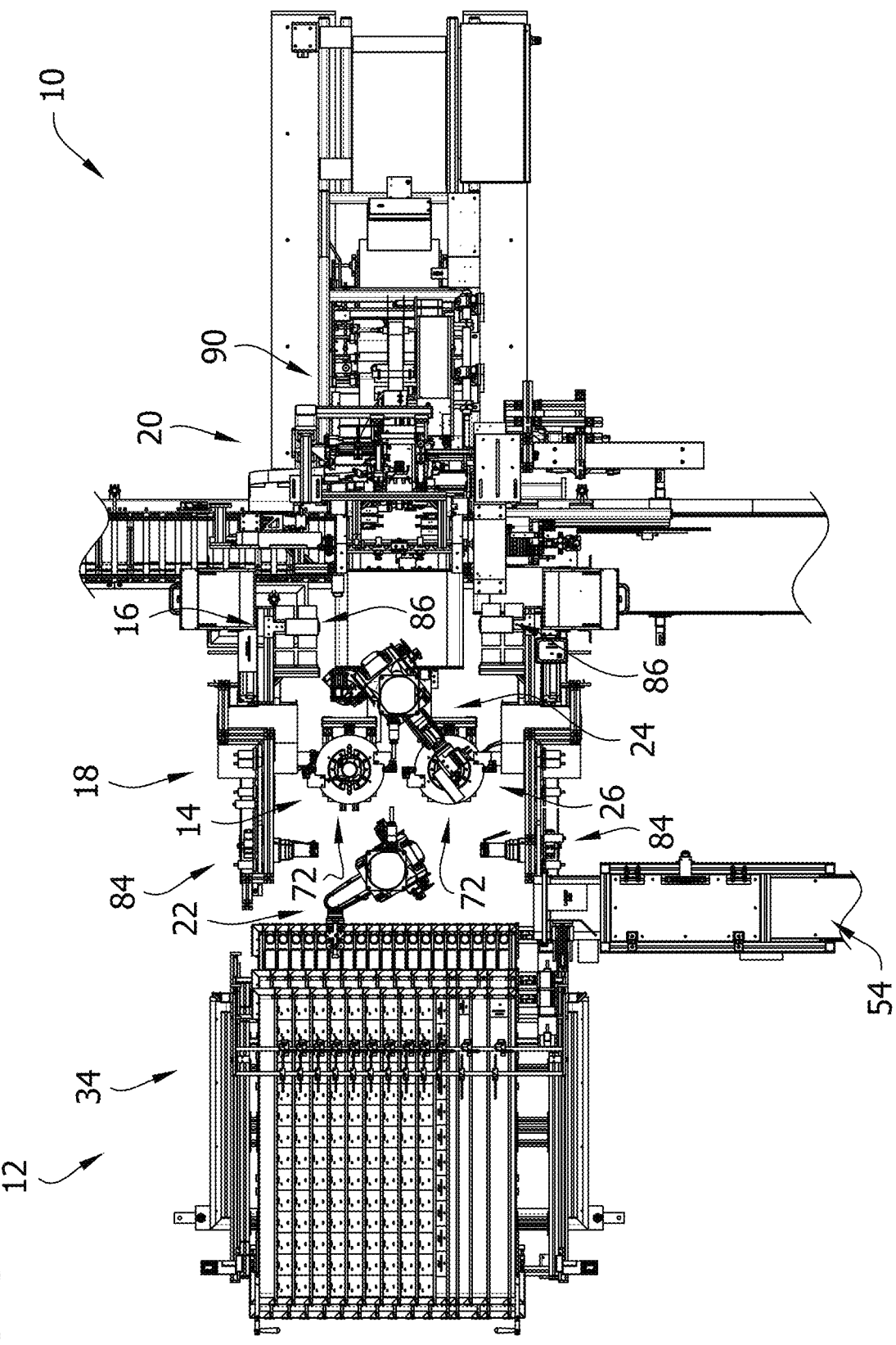
FIG. 5 is top view of the pharmaceutical container processing system of FIG. 4, with an enclosure and a frame hidden from view to reveal interior details.
Figure 7:
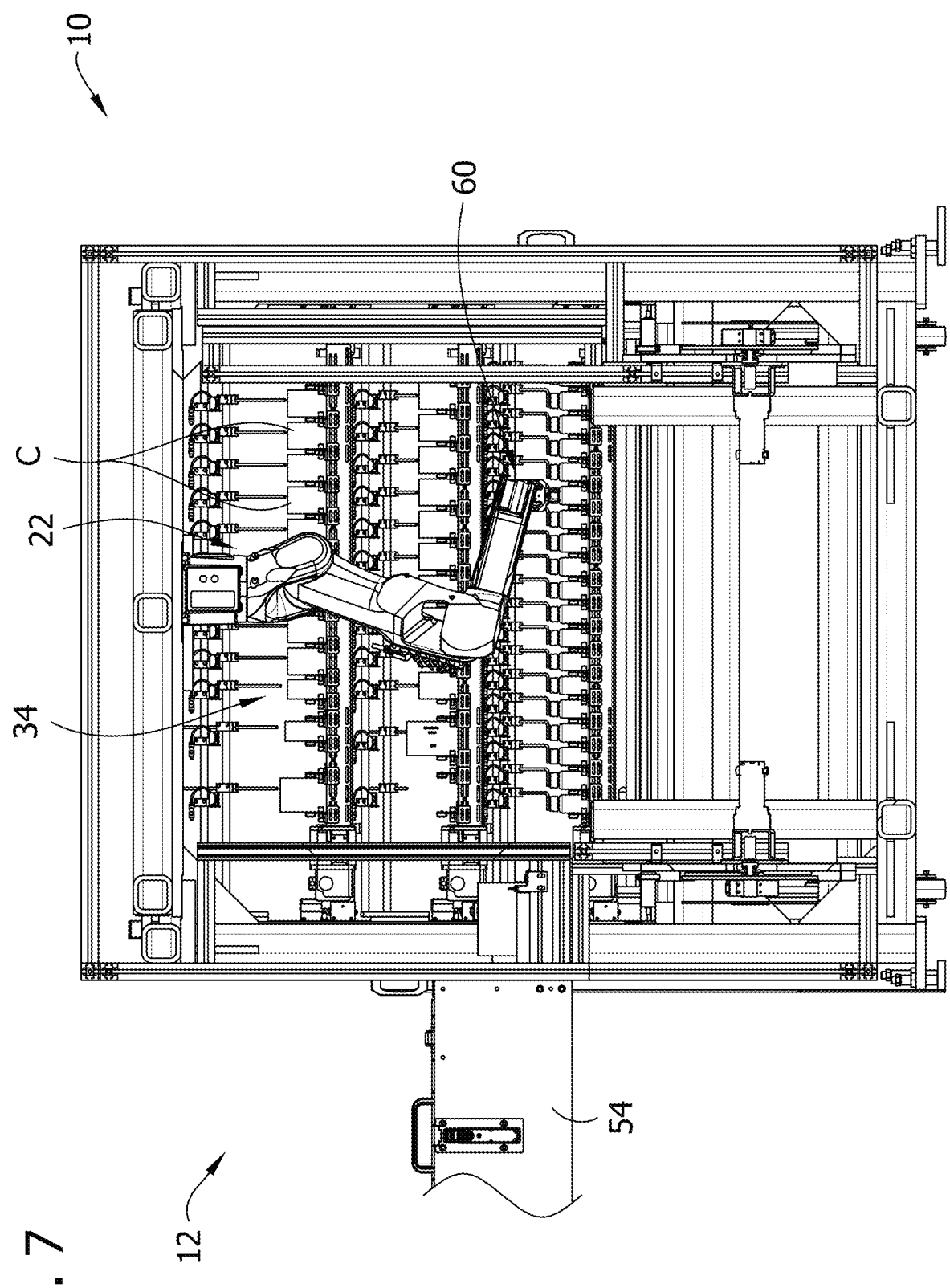
FIG. 7 is cross-section of the pharmaceutical container processing system of FIG. 4 looking at a first container repository of the system.
Figure 8:
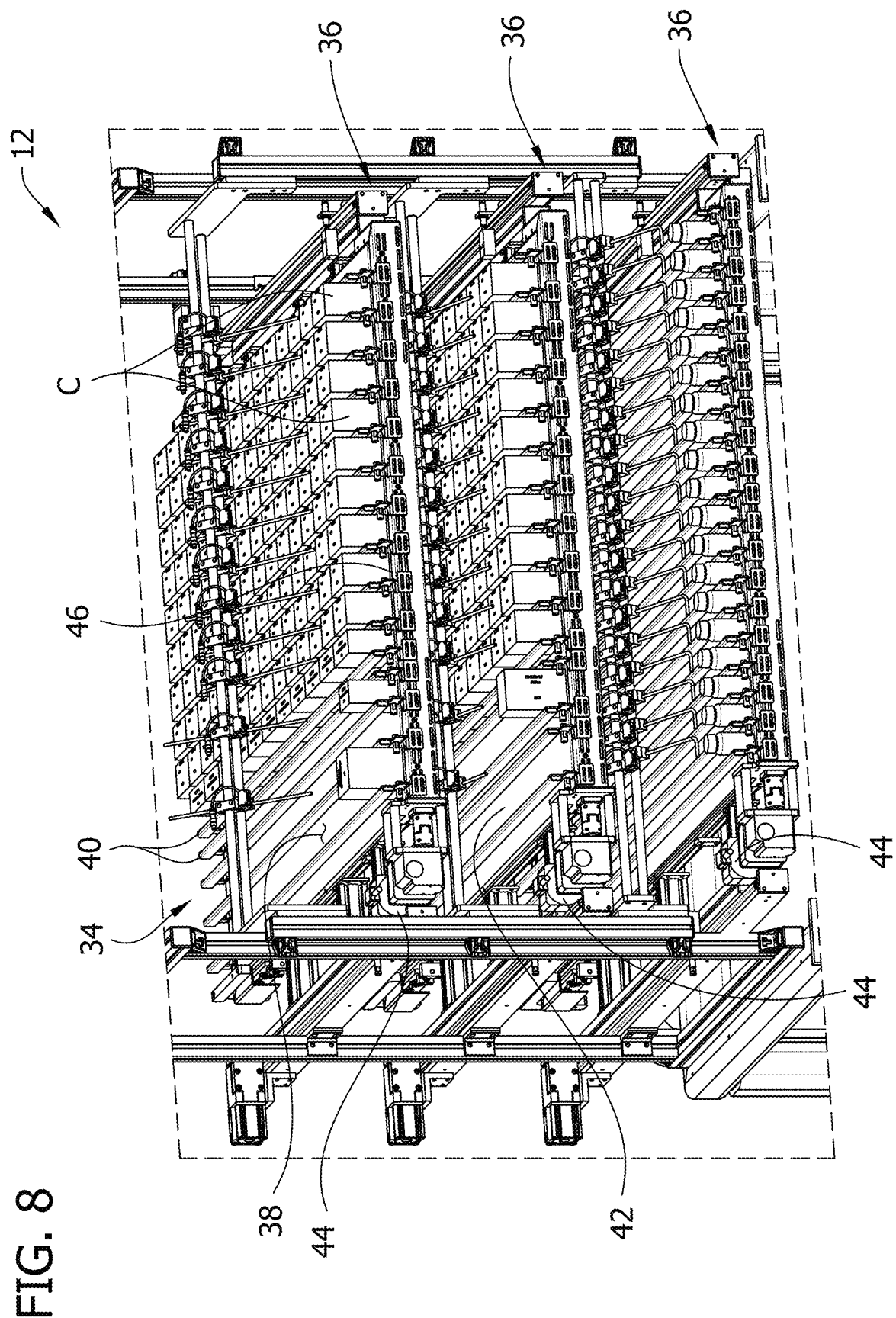
FIG. 8 is an enlarged perspective of the first container repository.

Referring to FIGS. 5-7, the first container transporter 22 is configured to grab the container C from the first repository 34 and the second repository conveyor 54. The first container transporter 22 is supported by (e.g., mounted to) a frame 58 (FIG. 4). Specifically, the first container transporter 22 is suspended from the frame 58. In the illustrated embodiment, the first container transporter 22 comprises a robot such as a six-axis robotic arm, although other robots are within the scope of the present disclosure. For example, the first container transporter 22 may comprise a selective-compliance-articulated robotic arm, a cylindrical robot, a delta robot, a polar coordinate robot, a vertically articulated robot, a Cartesian coordinate robot or any other suitable device. The first container transporter 22 includes a gripper 60 configured to grip the container C. The gripper 60 may include movable jaws, a suction pad, a suction bag (e.g., a bag with suction inlets and filled with beads that conforms to the shape of the container C) or any other suitable mechanism for gripping the containers C. The gripper 60 pick up or grabs the containers C. The gripper 60 may include two or more grippers, each for gripping a different type of container C. For example, the gripper 60 may include a first gripper (e.g., jaws, fingers) for gripping the cap of a bottle-shaped container and a second gripper (e.g., a suction bag or pads) for gripping a box-shaped container. The first container transporter 22 can switch between the different grippers depending on the type of container C being grabbed. For example, the gripper 60 may be rotatable relative to the rest of the first container transporter 22 such that it can selectively rotate the first and second grippers into an operational position, where the respective first or second gripper is able to engage a pharmaceutical container.

The first container transporter 22 moves the container C to the transfer station 26. The first container transporter 22 may move the container C to other stations before delivering the container to the transfer station 26. In the illustrated embodiment, the first container transporter 22 moves the container C from the storage station 12 (e.g., first repository 34 or second repository conveyor 54) directly to the transfer station 26. As will become apparent, the container C generally moves from the storage station 12 to the first identification station 14, then to the labeling station 18, then to the second identification system 16 and then to the outlet station 20. It is understood that the transfer station 26 can be arranged to receive the container C between any one of these stations or at any intermediate station. An intermediate station is station between the storage station 12 (e.g., beginning station) and the outlet station 20 (e.g., ending station) such as the first identification station 14, the labeling station 18, and the second identification system 16.

Referring to FIGS. 5, 6, 9 and 10, the system 10 includes one or more holders 62 (e.g., container holders) at the transfer station 26. The first container transporter 22 moves the picked container C to one of the holders at the transfer station 26. In the illustrated embodiment, the system 10 includes two holders 62 (e.g., first and second holders) at the transfer station 26. Having two holders 62 increase the efficiency of the system 10 by allowing the first container transporter 22 to be placing a container C on one holder while the second container transporter 24 is removing a container from the other holder. In this manner, there is generally always an empty holder 62 able to receive a container C from the first container transporter 22. The two holders 62 are identical. Accordingly, one holder 62 will now be described with the understanding the description applies equally to the other holder. The holder 62 facilitates the transfer of the container C from the first container transporter 22 to the second container transporter 24. The holder 62 is configured to receive and hold a pharmaceutical container C from the first container transporter 22 and to permit the second container transporter 24 to grab and remove the held container from the holder. In other words, the holder 62 is configured to hold a pharmaceutical container C while said pharmaceutical container is transferred (e.g., exchanged) from the first container transporter 22 to the second container transporter 24.

In the illustrated embodiment, the holder 62 includes a base 64 supporting a platform 66 (e.g., plate, pad) that defines a support surface (e.g., an upper surface of the platform) on which the first container transporter 22 places the pharmaceutical container C. Desirably, the holder 62 is configured to hold (e.g., grip) the pharmaceutical container C. In the illustrated embodiment, the holder 62 is configured to apply suction to the container C to hold the container on the holder. The system 10 can includes a negative pressure source 70 (FIG. 17), such as a vacuum, fluidly coupled to the holder 62 to apply the suction to hold the container C. In the illustrated embodiment, the platform 66 includes (e.g., defines) one or more openings or apertures 68 (e.g., vacuum ports, inlets) in the support surface that are fluidly coupled to the negative pressure source 70. The negative pressure source 70, via the openings 68, applies suction to the pharmaceutical container C to hold the container on the support platform 66. This way, the holder 62 inhibits the pharmaceutical container C from moving after the holder receives the pharmaceutical container from the first container transporter 22. Desirably, the flow of negative pressure will be interrupted or stopped (e.g., interrupt the flow from the negative pressure source or turn off the negative pressure source 70) to allow the second container transporter 24 to remove the container C from the holder 62. In another embodiment, the holding force generated by the suction is not so large as to prevent the second container transporter 24 from removing the container C from the holder 62. This way the second container transporter 24 can apply a sufficient amount of force to overcome the suction force to remove the container C from the holder 62 without having to reduce, interrupt or stop the supply of suction. In one embodiment, the holder 62 is configured to rotate the container C while the container is held by the holder. For example, the platform 66 supporting the container C may be rotatable relative to the base 64.

By moving the container C to the transfer station (e.g., placing the container on the holder 62) with the first container transporter 22 and then moving the container C from the transfer station with the second container transport 22, the cycle time for the system 10 to process a container is reduced, allowing the system to process more pharmaceutical containers in a given time frame. The first container transporter 22 is able to move a first container C along (e.g., to, from, between, through, etc.) a first subset of stations (e.g., storage station 12) while the second container transporter 24 is able to simultaneously move a second container along a second subset of stations (e.g., labeling station 18, second identification station 16 and outlet station 20). In the illustrated embodiment, the transfer between the first container transporter 22 and the second container transporter 24 at the transfer station 26 is before the labeling station 18. However, as explained above, it is understood that the transfer at the transfer station could occur at other positions along the set of container operation stations.

Referring to FIGS. 5, 6, 9 and 10, system 10 includes a first identification system 72 at the first identification station 14. In the illustrated embodiment, the system 10 includes two first identification systems 72 at the first identification station 14. Each first identification system 72 corresponds to one of the holders 62. The two first identification systems 72 are identical. Accordingly, one first identification system 72 will now be described with the understanding the description applies equally to the other first identification system. The first identification system 72 is configured to identify the container C. The first identification system 72 is arranged to identify the container C after the container has been removed from the storage station 12 but before a new label is applied at the labeling station 18. This way the system 10 can confirm it (e.g., the first container transporter 22) removed the correct container C (e.g., the container with the correct type of prescription for the prescription order) from the storage station 12 before the new label is applied.

As illustrated, the holder 62 and the first identification system 72 are proximate to one another. In fact, the holder 62 supports the first identification system 72. Accordingly, the transfer station 26 and the first identification station 14 are generally coincident with one another. Thus, when the first container transporter 22 moves the picked container C to the holder 62 at the transfer station 26, the first container transporter is also moving the container C to the first identifications system 72 at the first identification station 14. Likewise, when the second container transporter 24 moves the container C from the holder 62 at the transfer station 26, the second container transporter is also moving the container from the first identification system 72 at the first identification station 14.

The first identification system 72 is configured to identify the container C while the container is on (e.g., being held by) the holder 62. This way, the container C can be identified while the container is being transferred from the first container transporter 22 to the second container transporter 24. Transferring and identifying the container C generally simultaneously reduces the overall cycle time it takes the system 10 to process the container.

In the illustrated embodiment, the first identification system 72 includes one or more identifiers 74 (e.g., first identifiers) configured to identify the container C. Each identifier 74 is configured to scan (e.g., read) a label (e.g., a manufacture's label) on the container C to identify the container C. Each identifier 74 comprises an identification sensor configured to scan the container C to verify the identity of the container. The identification sensor can read or scan a machine readable marking (e.g., a barcode, QR code, etc.) or an identification chip (e.g., a near field communication (NFC) chip, a radio frequency identification (RFID) tag, or other similar devices) on the container C. By reading the machine readable marking or identification chip on the pharmaceutical container C, the identity or type of the pharmaceutical container can be verified or confirmed to ensure the correct pharmaceutical container was removed from the storage station 12. The identification sensor may comprise a camera, a barcode scanner, identification tag reader (e.g., NFC reader, RFID reader, etc.) or any other suitable device. Other configurations of the identifier are within the scope of the present disclosure.

In the illustrated embodiment, each identifier 74 is configured to rotate relative to (e.g., about) the container C as the container is held by the holder 62. The first identification system 72 includes a turntable 76 mounted on the holder 62. Two identifier supports 78 are positioned on generally opposite sides of the turntable 76. Two identifiers 74 are mounted to each identifier support 78. The two identifiers 74 on each identifier support 78 are vertically spaced apart to scan different vertical areas of the container C to ensure at least one of the identifiers will read the machine readable marking on the label—regardless of the vertical position of the machine readable marking. The four identifiers 74 (two on each identifier support 78) face towards a rotation axis of the turntable 76. The rotation axis of the turntable 76 is generally aligned with the platform 66 of the holder 62 such that the container C held thereon is generally aligned with the rotation axis. Accordingly, the identifiers 74 face the container C held on the holder 62. The turntable 76 rotates the identifiers 74 about the container C (e.g., rotation axis) to read the machine readable marking on the container, regardless of the initial orientation of the machine readable marking relative to the identifiers when the container C is placed on the holder 62. The first identification system 72 may include a prime mover 80 (FIG. 17), such as an electric motor or solenoid, operatively coupled to the turntable 76 for rotating the turntable (broadly, the prime mover is operatively connected to the identifiers for moving the identifiers relative to the container C). In one example, the turntable 76 may rotate the identifiers 74 approximately 180 degrees about the container C. As a result, 360 degrees of coverage for the pharmaceutical container C is obtained, ensuring at least one of the four identifiers 74 will read the machine readable marking on the container. Other configurations of the first identification system are within the scope of the present disclosure. Broadly, at least one of the holder 62 is configured to rotate the container C relative to each identifier 74 and/or the identifier is configured to rotate about the container. For example, in other embodiments, the identifiers 74 are stationary and the holder rotates the container C or the holder rotates the container C while the identifiers are also simultaneously rotating (in the opposite direction).

Referring to FIGS. 5, 6 and 9-11, the second container transporter 24 is configured to grab the container C from the transfer station 26 (e.g., one of the holders 62). The second container transporter 24 is supported by (e.g., mounted to) the frame 58 (FIG. 4). Specifically, the second container transporter 24 is suspended from the frame 58. In the illustrated embodiment, the second container transporter 24 comprises a robot such as a six-axis robotic arm, although other robots are within the scope of the present disclosure. For example, the second container transporter 24 may comprise a selective-compliance-articulated robotic arm, a cylindrical robot, a delta robot, a polar coordinate robot, a vertically articulated robot, a Cartesian coordinate robot or any other suitable device. The second container transporter 24 includes a gripper 82 (FIG. 10) configured to grip the container C. The gripper 82 may include movable jaws or fingers, a suction pad, a suction bag (e.g., a bag with suction inlets and filled with beads that conforms to the shape of the container C) or any other suitable mechanism for gripping the containers C. The gripper 82 pick up or grabs the containers C. The gripper 82 of the second container transporter 24 can be identical to the gripper 60 of the first container transporter 22. For example, the gripper 82 can include two or more grippers for different types of containers, as explained above. In the illustrated embodiment, the first and second container transporters 22, 24 are generally identical.

The second container transporter 24 moves the container C from the transfer station 26 (and the first identification station 14 in the illustrated embodiment) to the outlet station 20. The second container transporter 24 may move the container C to other stations before delivering the container to the outlet station 20. In the illustrated embodiment, before the container C is moved to the outlet station 20, the second container transporter 24 moves the container C along the labeling station 18 and the second identification station 16.

Accordingly, the first container transporter 22 moves the pharmaceutical containers C through a portion of the set of container operation stations and the second container transporter 24 moves the pharmaceutical containers through another portion of the set of container operation stations generally simultaneously. In the illustrated embodiment, the first container transporter 22 moves the pharmaceutical containers C from the storage station 12 and to the first identification station 14 and the transfer station 26 and the second container transporter 24 moves the container from the first identification station and transfer station, along the labeling station 18, the second identification station 16 and then to the outlet station 20. It is understood the first and second container transporters 22, 24 may move the containers C along other stations.

Figure 9:
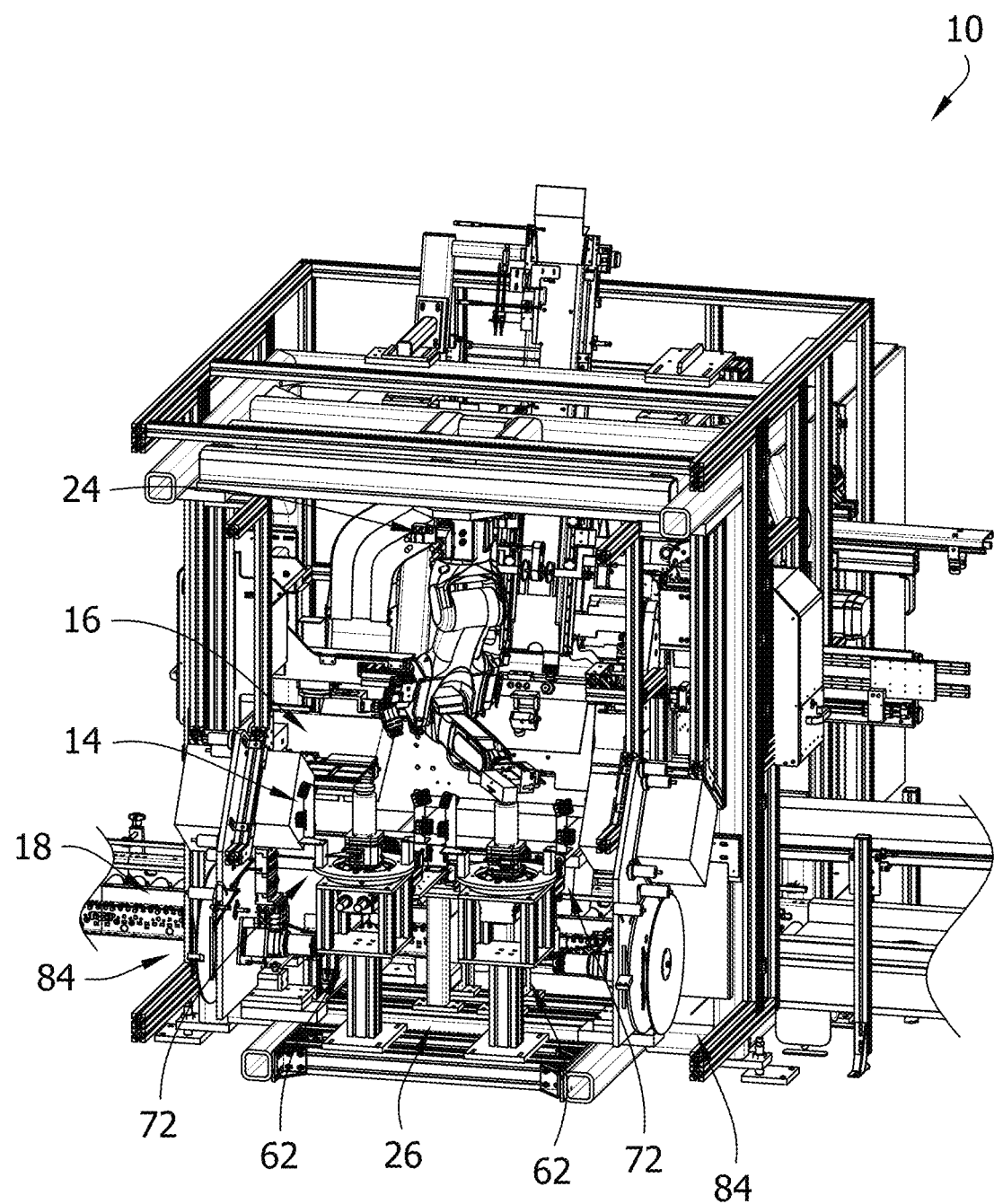
FIG. 9 is a cross-section perspective of the pharmaceutical container processing system of FIG. 4 looking at a transfer station of the system.
Figure 10:
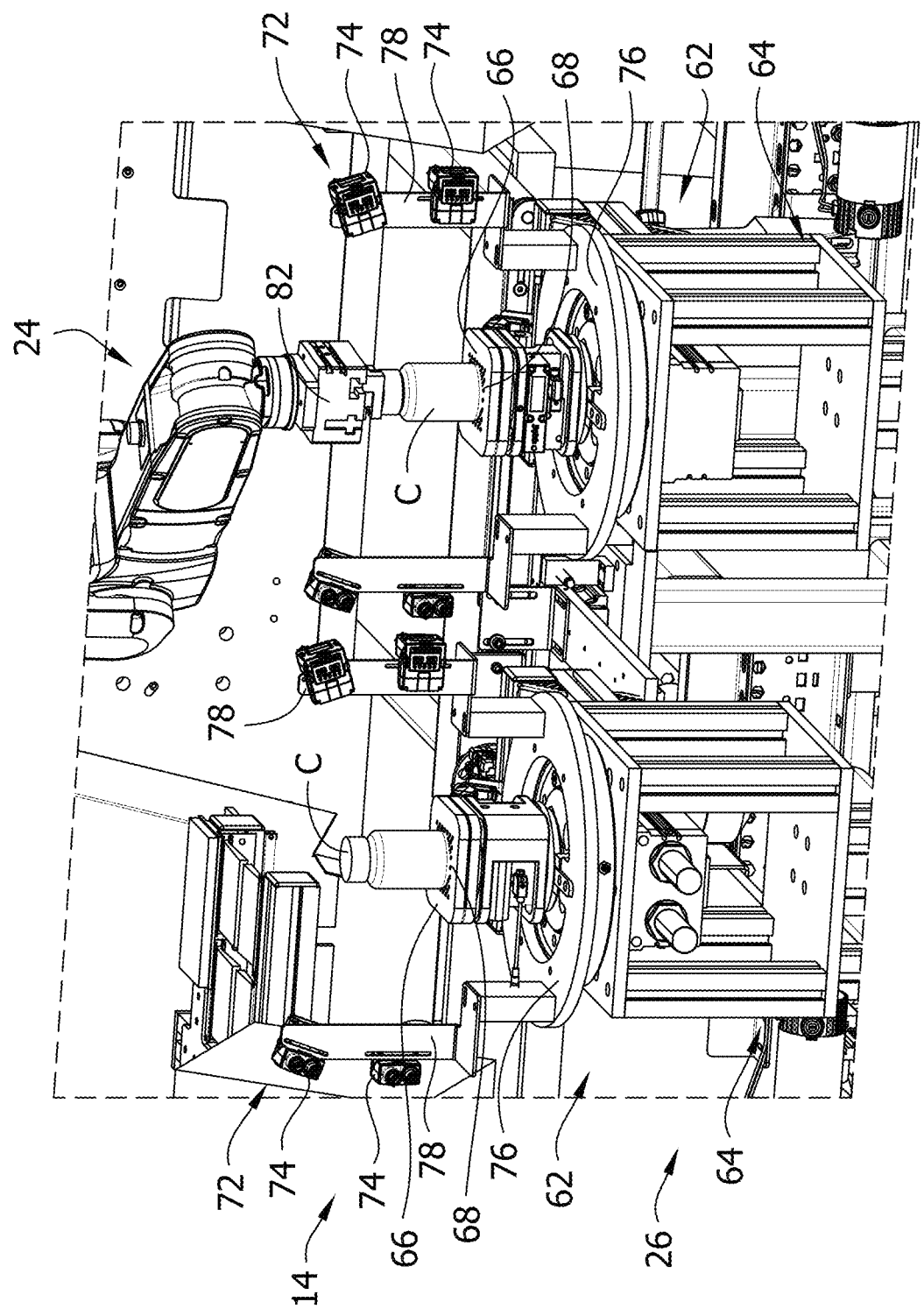
FIG. 10 is an enlarged perspective of the transfer station.
Figure 11:
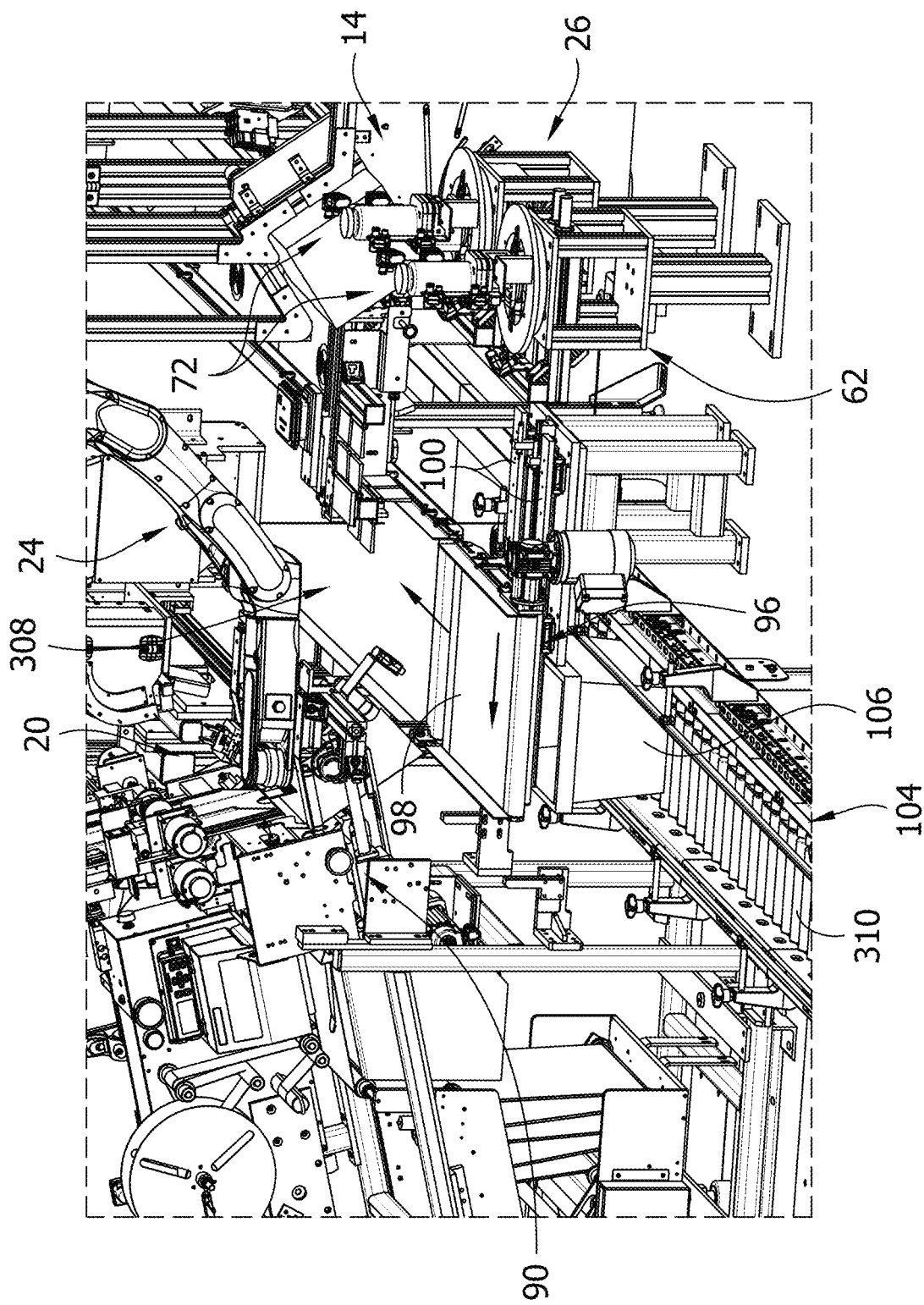
FIG. 11 is a perspective of an outlet station of the pharmaceutical container processing system of FIG. 4 with a collector in a collection position and the enclosure and frame hidden from view to reveal interior details.

Referring to FIGS. 5, 6 and 9, the system 10 includes one or more labelers 84 at the labeling station 18. In the illustrated embodiment, the system 10 includes two labelers 84 at the labeling station 18. Each labeler 84 corresponds to one of the holders 62 and first identification systems 72. The two labelers 84 are generally identical. Accordingly, one labeler 84 will now be described with the understanding the description applies equally to the other labeler. The labeler 84 is configured to apply a label (e.g., a patient specific label) to the pharmaceutical container C. In one embodiment, the labeler 84 may print and then apply the label to the pharmaceutical container C. The labeler 84 applies the label after the identity of the container C has been confirmed by the first identification system 72. Labelers are generally known in the art, and thus a further description of the labeler is omitted herein. For example, the labeler 84 may be a pass through labeler that applies the label to the pharmaceutical container C as the container is moved through the labeler by another component. In this embodiment, the second container transporter 24 moves the container C to and along (e.g., through) the labeler 84. As the second container transporter 24 moves the container C along the labeler 84, the labeler applies the patient specific label to the container C (generally over the existing manufacturer's label).

As illustrated, the labeler 84 is adjacent to one of the holder 62 and first identification system 72 sets. Accordingly, the second container transporter 24 only moves the container a short distance between the holder 62 and the labeler 84, minimizing the time required to process the container. In other embodiment, the system 10 may only include a single holder 62 for both holder 62 and first identification system 72 sets.

Referring to FIG. 5, the system 10 includes a second identification system 86 at the second identification station 16. In the illustrated embodiment, the system 10 includes two second identification systems 86. Each second identification system 86 corresponds to one of the labelers 84. The two second identification systems 86 are identical. Accordingly, one second identification system 86 will now be described with the understanding the description applies equally to the other second identification system. The second identification system 86 is configured to identify the container C. Specifically, the second identifications system 86 is arranged to identify the container C after the label has been applied by the labeler 84. This way, the system 10 can confirm the correct label was applied to the container C by the labeler 84. The second identification system 86 includes one or more identifiers 88 (FIG. 17) configured to identify the container C. Specifically, the identifiers 88 are configured to read or scan a machine readable marking on the label applied by the labeler 84 to confirm the identity of the container C (e.g., label) and that the correct label was applied. The identifiers 88 are generally the same as the identifiers 74 described above. In the illustrated embodiment, the identifiers 88 of the second identification system 86 are in a stationary or fixed position. Accordingly, as second container transporter 24 moves the container C along the second identification system 86, the container is moved pass the one or more identifiers 88 to have the identifiers read the label.

As illustrated, the second identification system 86 is adjacent one of the labelers 84. Accordingly, the second container transporter 24 only moves the container C a short distance between the labeler 84 and the second identification system 86, minimizing the time required to process the container. In other embodiments, the system 10 may only include a single second identification system 86 for both labelers 84 or only the embodiments with only one labeler.

Referring to FIGS. 5, 6, 11 and 12, the system 10 includes a packager or bagger 90 at the outlet station 20. The bagger 90 (broadly, a shipping preparation device) can be any suitable device for bagging, packaging, sealing, boxing, etc., one or more containers C for shipping the containers to the patient. The bagger 90 is configured to package or bag one or more pharmaceutical containers C in a package (e.g., bag). The bagger 90 is configured to receive the container C directly from the second container transporter 24. That is the second container transporter 24 delivers the container to the bagger 90. The second container transporter 24 may generally drop the container C into the bagger 90. The bagger 90 generally prepares the container C for shipping to the patient. The bagger 90 may include a bagger identification system (similar to the identification systems described herein) for confirming the identity of the pharmaceutical container C before the second container transporter 24 drops the pharmaceutical container into the bagger.

As mentioned above, the pharmaceutical order processing system 300 includes a literature processor 312 configured to supply (via the literature conveyor 314) the system 10 (specifically, the bagger 90) with the literature corresponding to the prescription order for packaging with the pharmaceuticals containers C. The literature processor 312 may include a printer (not shown) to create the literature. The literature may be in the form of a slip, sheet, pamphlet, book, and the like and may contain information (e.g., directions) related to the pharmaceuticals in the pharmaceutical container and/or other information (e.g., patient information) related to the prescription order. When packing the pharmaceutical containers C, the bagger 90 can also pack the corresponding literature (e.g., a literature pack) for the pharmaceutical containers C in the shipping package. In one embodiment, the system 10 may include its own literature processor.

The bagger 90 is configured to pack the pharmaceutical container(s) C and literature of a prescription order in a package (not shown) for shipment. The package may be a box, a bag or any other suitable delivery package. The bagger 90 comprises a pre-formed bag bagger, a wrap seal bagger, or any other suitable device. If a prescription order requires two or more pharmaceutical containers C to fill the prescription order, the bagger 90 can receive the two or more containers, one at a time, from the second container transporter 24 to consolidate (e.g., combine, marry) the two or more pharmaceutical containers C (and corresponding literature) into the same shipping package. After the bagger 90 receives the one or more pharmaceutical containers C of a prescription order from the second container transporter 24, the bagger packages the pharmaceutical containers and corresponding literature in the package. The bagger 90 may also label the package with the patient's name and address. Baggers 90 and literature processors 312 are generally known in the art and thus a detailed description is omitted herein. In the illustrated embodiment, the system 10 includes one bagger 90 and corresponding literature processor 312, although more or fewer baggers and literature processors are within the scope of the present disclosure.

The system 10 (broadly, the pharmaceutical order processing system 300) may also include a literature reader or scanner 94 (FIG. 17) configured to read the literature. The literature reader 94 may read a machine readable marking (e.g., barcode, QR code, etc.) of the literature. The literature reader 94 may read the literature to build the prescription order. For example, the system 10 may select a container C for processing from the storage station 12 based on the read literature by the literature reader 94, as described in more detail below. The literature processor 312 may also fold, staple and/or otherwise prepare the literature for inclusion with the pharmaceutical container(s) C in the package. After the package is prepared by the bagger 90, the package is ready to be shipped to the patient.

Other components may be disposed at the outlet station 20 for receiving the container C from the second container transporter 24. For example, a conveyor system (not shown) may be positioned to receive the container C directly from the second container transporter 24. The conveyor system can then transport the container C to another portion of the pharmacy for further processing, such as marrying with other containers from other pharmaceutical container processing systems.

The bagger 90 may also receive pharmaceutical containers C from other sources (e.g., secondary container processors) besides the second container transporter 24. This enables the pharmaceutical order processing system 300 to be able to marry or combine pharmaceutical containers C (e.g., unit-of-use product, auto-filled containers) from different sources (e.g., system 10, high-volume filler) into a single package for shipping to the patient. This allows for marrying or combining multiple containers from different sources in the same bag. These different sources can include other unit-of-use systems and/or high-volume filler systems. Other secondary container processors, such as those described in U.S. Pat. Nos. 9,937,100 and 8,892,245, are within the scope of the present disclosure and hereby incorporated by reference. In the illustrated embodiment, the bagger 90 can receive pharmaceutical containers C processed by a secondary container processor, such as a high-volume filler. As mentioned above, the pharmaceutical containers C from the high-volume filler are staged at the bottle table 302 and transported to the system 10 via the bottle table conveyor 306. In one embodiment, the bottle table 302 releases one or more pharmaceutical containers C to the system 10 based on the literature read by the reader 94. For example, the bottle table 302 may release one or more pharmaceutical containers C corresponding to a prescription order associated with the literature.

Figure 13:
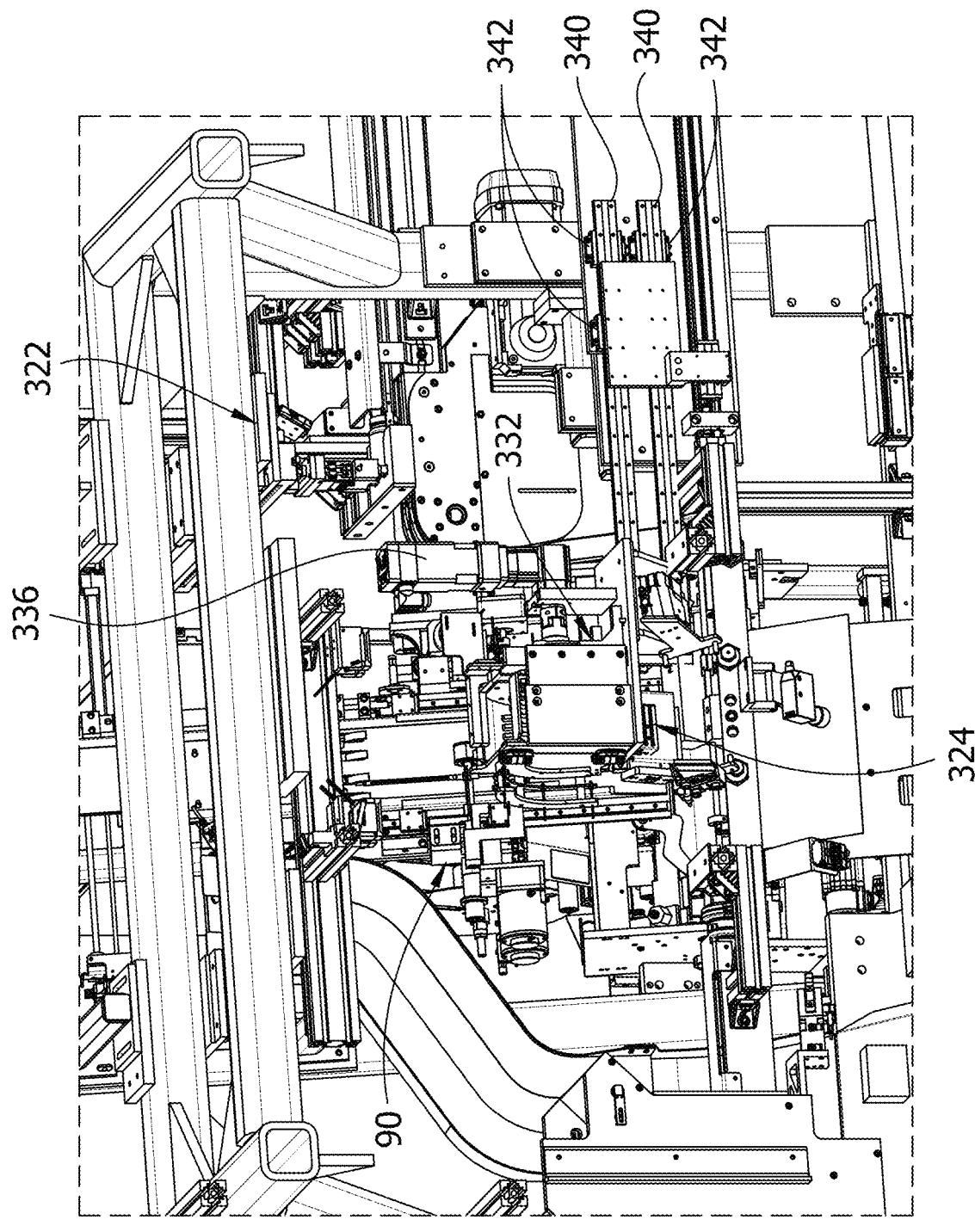
FIG. 13 is a perspective of the outlet station with a pharmaceutical container dispenser of the pharmaceutical order processing system in a dispensing position.
Figure 14:
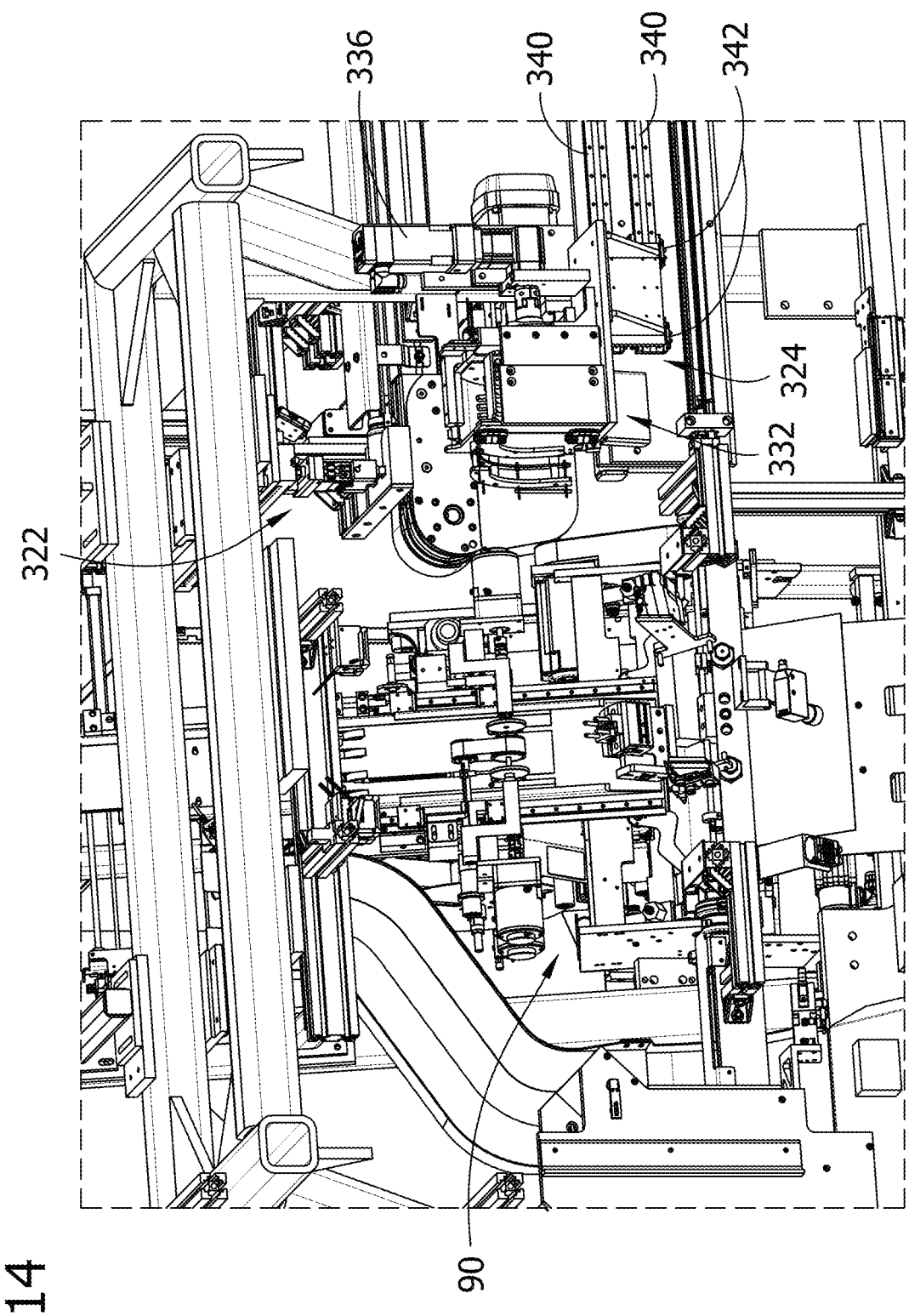
FIG. 14 is a perspective similar to FIG. 13, except the pharmaceutical container dispenser is in a receiving position.
Figure 15:
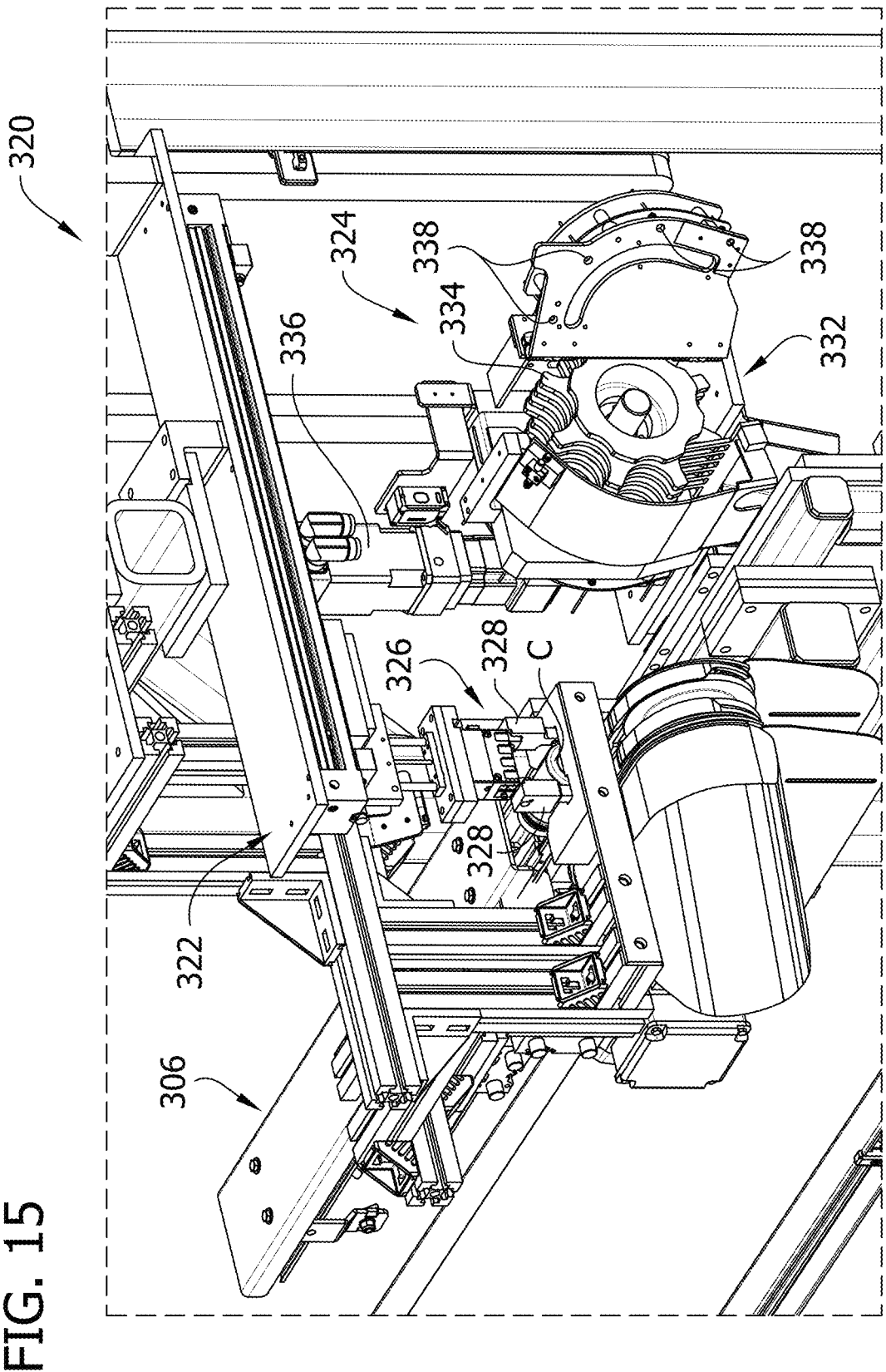
FIG. 15 is a rear perspective of the pharmaceutical container dispenser, with a door opened to reveal interior details, and a container transporter associated with the pharmaceutical container dispenser.

Referring to FIGS. 13-15, to transfer or place the pharmaceutical containers C from the bottle table conveyor 306 to the package at the bagger 90, the pharmaceutical order processing system 300 includes a container transporter system 320. The container transporter system 320 is configured to marry the pharmaceutical containers C. The container transporter system 320 may marry the containers C by delivering one or more containers to the bagger 90 that corresponds to (e.g., is to be married with) a container from the second container transporter 24. The container transporter system 320 includes a container transporter 322 and a pharmaceutical container dispenser 324 (broadly, also a container transporter). The container transporter 322 is configured to pick up the pharmaceutical container C from the bottle table conveyor 306 and place the pharmaceutical container in the pharmaceutical container dispenser 324. The container transporter 322 includes a gripper 326 with opposing movable jaws 328 for selectively grabbing and releasing the pharmaceutical container C. The gripper 326 is operatively coupled to two prime movers 330 (e.g., electric motors, linear actuators, etc.). One prime mover 330 raises and lowers the gripper and the other prime mover 330 translates the gripper between the bottle table conveyor 306 and the pharmaceutical container dispenser 324.

The pharmaceutical container dispenser 324 includes a holder 332 for holding and dispensing the pharmaceutical containers C. The holder 332 includes a housing that defines an interior. The holder 332 includes a rotatable wheel 334 (e.g., star wheel) for holding pharmaceutical containers C. The wheel 334 defines a plurality of container receiving spaces about the perimeter thereof, each space sized and shaped to receive one pharmaceutical container C. The housing of the holder 332 defines an inlet at an upper end thereof for container transporter 322 to insert a pharmaceutical container C into one of the container receiving spaces of the wheel 334. The housing of the holder 332 also defines an outlet at a lower end thereof for permitting a pharmaceutical container C to fall out of the holder (e.g., to be dispensed) when the container receiving space is aligned with the outlet. The wheel 334 rotates to move the pharmaceutical containers C toward the outlet. The wheel 334 is operatively connected to a prime mover 336 (e.g., electric motor) which can rotate the wheel by set increments to align a container receiving space with the inlet or outlet. The combination of the housing and the wheel 334 secures the pharmaceutical containers C in the respective container receiving spaces as the wheel rotates. The pharmaceutical container dispenser 324 may include container sensors 338 (e.g., proximity sensors) for detecting the presence of the pharmaceutical containers C in the container receiving spaces. The sensors 338 are arranged on the housing (e.g., a door thereof) such that they align with the container receiving spaces when one container receiving space is aligned with the inlet and another container receiving space is aligned with the outlet. The sensors 338 are used to confirm when a pharmaceutical container C has been received by the holder 332 and dispensed from the holder. The container transporter system 320 may also include an identification system (like the identification systems described herein) for confirming the identity of the pharmaceutical container C before the container is placed in the holder 332. In one embodiment, because the rotational orientation of the pharmaceutical container C relative to the container transporter system 320 will be generally random when the container is delivered via the bottle table conveyor 306, the pharmaceutical container may have a plurality (e.g., 4, 8, 10, 12, 13 or more) of machine readable markings spaced around the container so that the identification system can conform or validate the container regardless of the orientation of the container. The plurality of machine readable markings can be applied by the container processor that processed the pharmaceutical container C, such as the high-volume filler.

The holder 332 is moveable between a retracted or receiving position (FIG. 14) and an extended or dispensing position (FIG. 13). In the receiving position, the holder 332 is arranged to receive a pharmaceutical container C from the container transporter 322. Specifically, the inlet of the holder 332 is in a position that the gripper 326 can be aligned (e.g., horizontally and vertically aligned) with so that the gripper can place the pharmaceutical container C in one of the container receiving spaces. In the dispensing position, the holder 332 is arranged to dispense the pharmaceutical container C to the bagger 90. Specifically, the outlet of the holder 332 is in a position such that when a pharmaceutical container C moves (e.g., falls) through the outlet, the pharmaceutical container is received by the bagger 90 (e.g., falls into the package held by the bagger). When in the dispensing position, the wheel 334 rotates to dispense one or more pharmaceutical containers C. In the illustrated embodiment, the holder 332 is supported by rails 340. The rails 340 are mounted to slides 342 that permit the rails to move (e.g., slide) therein. The rails 340 move (e.g. slide) relative to the slides 342 as the holder is moved between the receiving and extended positions. A prime mover 344 (e.g., electric motor, linear actuator) is operatively coupled to the one or both of the rails 240 to move the rails, and thereby the holder 332. Other configurations of the container transporter system 320 are within the scope of the present disclosure.

Figure 12:
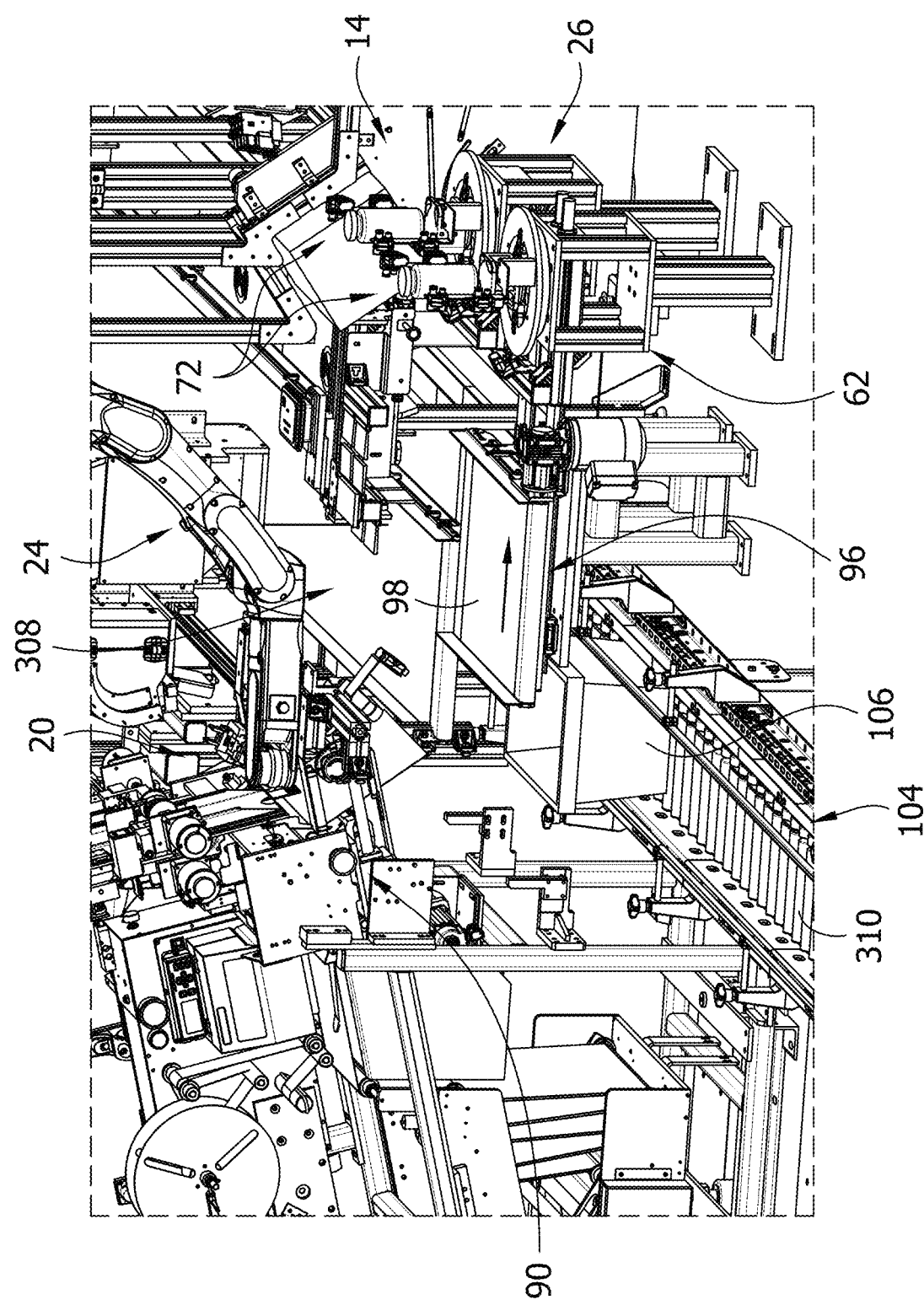
FIG. 12 is a perspective similar to FIG. 9, except the collector is in a clearance position.

Referring back to FIGS. 9 and 10, in the illustrated embodiment, the system 10 includes a collector 96 (e.g., a primary collector) at the outlet station 20. The collector 96 is configured to receive the package from the bagger 90. In the illustrated embodiment, the collector 96 is also configured to transport the package away from the bagger 90. For example, the collector 96 can move the package toward a mail processing area to be shipped to the patient. The collector 96 is movable between an extended or collection position (FIG. 11) and a retracted or clearance position (FIG. 12). In the collection position, the collector 96 is arranged to receive packages from the bagger 90. Specifically, the collector 96 is arranged to receive a package dropped by the bagger 90. In the collection position, the collector 96 is aligned with the package conveyor 308 and transfers the package to this conveyor which then coveys (e.g., moves) the package toward a processing area (e.g., mail processing area). In the clearance position, the collector 96 is arranged to not receive packages from the bagger 90.

In the illustrated embodiment, the primary collector 96 comprises a conveyor 98. The conveyor 98 is mounted on one or more movable rails 100. A prime mover 102 (FIG. 17), such as an electric motor or linear actuator, is operatively connected to the conveyor 98 to move the conveyor between the collection and clearance positions.

The system 10 may also include a secondary collector 104 at the outlet station 20. The secondary collector 104 is also configured to receive packages from the bagger 90. Specifically, the secondary collector 104 is arranged to receive packages from the bagger 90 when the primary collector 96 is in the clearance position. When the primary collector 96 is in the clearance position, the primary collector is arranged to permit the packages dropped by the bagger 90 to pass thereby and into the secondary collector 104. In the illustrated embodiment, the secondary collector comprises the collection bin 106 on the bin conveyor 310. The collection bin 106 may collect one or more packages from the bagger 90 and then be used to transport the packages to another area for further processing, such as marrying up with other packages and/or containers. Other arrangements are within the scope of the present disclosure.

Figure 17:
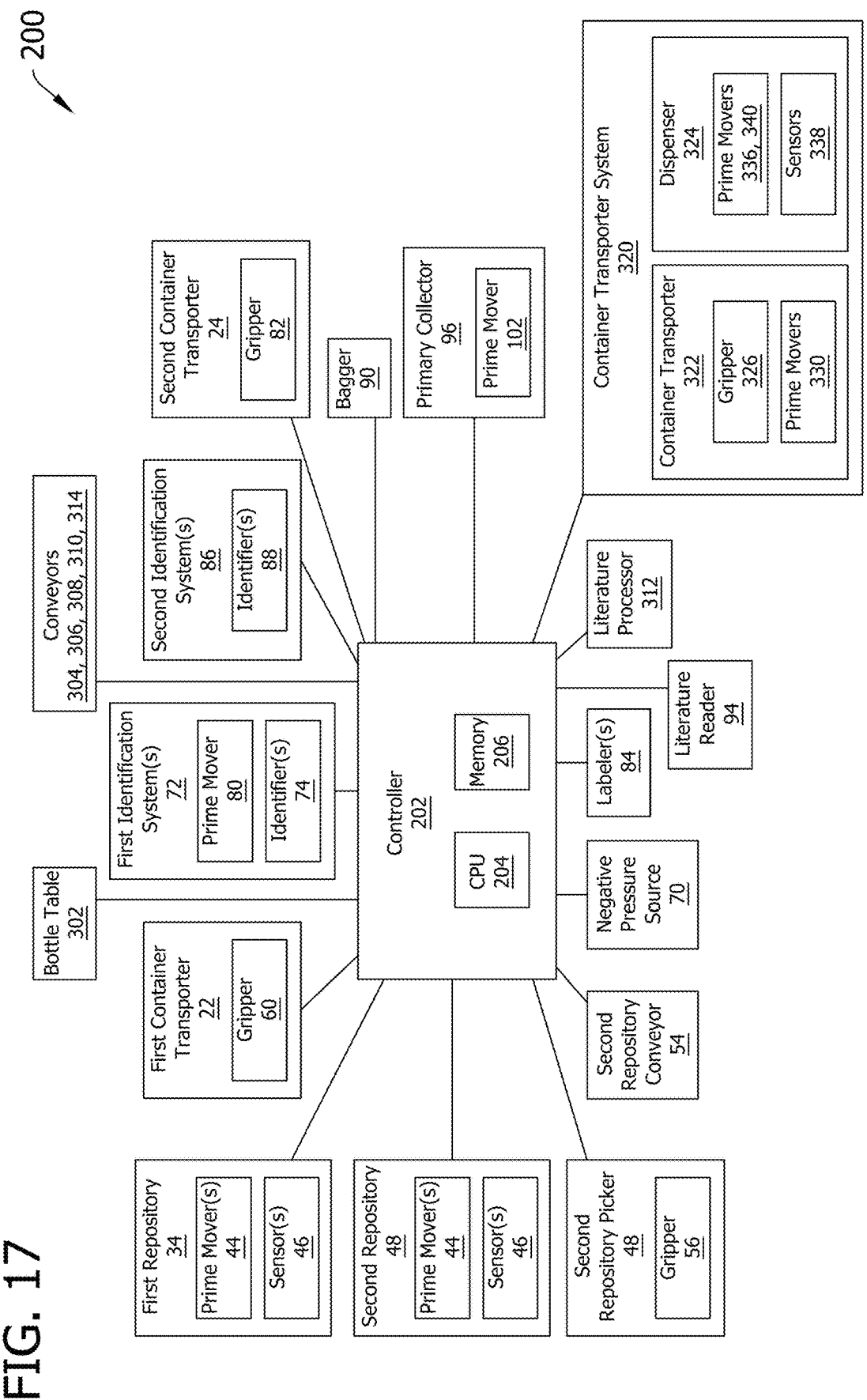
FIG. 17 is a schematic diagram of an example control system for the pharmaceutical container processing system of FIG. 4.

Referring to FIG. 17, an example control system (e.g. pharmaceutical container processing system control system) of the system 10 is generally indicated by reference numeral 200. The control system 200 includes a controller 202 (broadly, a computer) for controlling and operating the system 10 and its components. The controller 202 includes a CPU or processor 204 (e.g., a pharmaceutical container processing system processor) and RAM or memory 206 (broadly, non-transitory computer readable storage medium). The controller 202 directs (e.g., controls and operates) the various components (e.g., the first repository 34, the first container transporter 22, etc.) and sub-components (e.g., prime movers 44, etc.) thereof. Broadly, the memory 206 includes (e.g., stores) processor-executable instructions for controlling the operation of the system 10 and the components thereof. The instructions embody one or more functional aspects of the system 10 and components thereof (as described herein), with the processor 202 executing the instructions to perform said one or more functional aspects. The components of the system 10 may be in wired or wireless communication with the controller 202. The controller 202 may be a dedicated controller for the system 10 that is in communication with a control system of the pharmacy, the controller for the pharmaceutical order processing system 300, or part of the control system of the pharmacy. Other configurations of the control system 200 are within the scope of the present disclosure.

The controller 202 is communicatively coupled to the various components of the system 10 to control and/or operate these components. The controller 202 is configured to receive a prescription order for a patient and to direct (e.g., operate), as described herein, the system 10 to fulfill the prescription order (e.g., prepare a package for shipping containing the one or more pharmaceutical containers C that the prescription order calls for). For example, the controller 202 can operate the first container transporter 22 to pick an appropriate container C from the first repository 34. In another example, the controller 202 can receive identifying information (e.g., a serial number) of the pharmaceutical container C from the first identification system 72 (e.g., identifiers 74) and compare the identifying information to the prescription order to verify whether or not the correct pharmaceutical container was selected from the first repository 34 by the first container transporter 22. If the wrong pharmaceutical container C was picked, the controller 202 may instruct the first or second container transporter 22, 24 to move the pharmaceutical container an alternative location (e.g., a removal location) due to the pharmaceutical container not being the correct type for the pharmaceutical order. The controller 202 may also provide information (e.g., patient name, prescription information, etc.) to the labeler 84 for the creation of the label for the pharmaceutical container C. The controller 202 can also direct the printer to prepare (e.g., print) the literature for a prescription order.

Other types of information can also be shared between the controller 202 and the components of the system 10. For example, the controller 202 can send the location of a particular type of pharmaceutical container C on the first repository 34 to the first container transporter 22. In this embodiment, the location of the pharmaceutical container C may be obtained by a user input device (not shown) communicatively coupled to the controller 202 or by an identification sensor (e.g., scanner) (not shown) communicatively coupled to the controller 202. In one embodiment, the controller 202 is configured to operate the first container transporter 22 to pick a pharmaceutical container C from the first repository 34 in response to information (e.g., prescription information) obtained by the reader 94. For example, in one embodiment, the reader 94 reads the printed literature from the literature processor 312 and then the controller 202 operates the components of the system 10 to deliver the one or more pharmaceutical containers C corresponding to the literature to the bagger 90. If the literature includes literature associated with a pharmaceutical container C stored in the first repository 34, the controller 202 can directs the system 10 to bring the pharmaceutical container from the first repository to the bagger 90. If the literature includes literature associated with a pharmaceutical container C stored in the second repository 48, the controller 202 can directs the system 10 to bring the pharmaceutical container from the second repository to the bagger 90. Similarly, if the literature includes literature associated with a pharmaceutical container C staged at the bottle table 302, the controller 202 can direct the bottle table 302, the bottle table conveyor 306, and the container transport system 320 to bring the pharmaceutical container to the bagger 90. In this case, the controller 202 may also instruct the high-volume filler to fill the pharmaceutical container with the appropriate type and quantity of pharmaceuticals. Accordingly, it is understood the controller 202 directs the components of the system 10 (broadly, the pharmaceutical order processing system 300) as necessary to perform the functions described herein.

Referring to FIG. 18, an example flow diagram illustrating one method of operation of the system 10 is generally indicated at reference numeral 400. Initially, at step 402, a prescription order is submitted, by a patient or a doctor, to the system 10 (e.g., controller 202) for fulfillment by the system. At step 404, the first container transporter 22 picks a pharmaceutical container C from the storage station 12 (e.g., first or second repository 34, 48) to fill the prescription order. This may include moving the container C from the second repository 48 to the processing area 32. The controller 202 may instruct the first container transporter 22 to grab a pharmaceutical container C in response to receiving the prescription order or in response to the literature processor 312. After the pharmaceutical container C is grabbed by the first container transporter 22, the first container transporter moves the pharmaceutical container to the transfer station 26 and first identification station 14. At step 406, the container C is placed on the holder 62 and then the first identification system 72 scans the container C. Once the identity of the container C is confirmed, the second container transporter 24 removes the container from the holder 62 and moves to the container to the labeler 84 at the label station 18 where the labeler applies the patient specific label at step 408.

At step 410, the second container transporter 24 moves the container C to the second identification system 86 at the second identification station 16. The second identification system 86 scans the container C to confirm the correct label was applied to the container. At step 412, the second container transporter 24 delivers the container C to the bagger 90 at the outlet station 20, which packages the container C. The package is then received by either the primary collector 96 or the secondary collector 104 before eventually being shipped to the patient at step 414. The operation 400 then repeats for the next prescription order (e.g., pharmaceutical container C). It is understood, that many of these processes or steps of operation 400 can happen simultaneously with different pharmaceutical containers C. For example, the bagger 90 can be packaging a first pharmaceutical container C, while the first container transporter 22 is delivering a second pharmaceutical container to the transfer station 26, and/or while the labeler 84 is applying a label to a third pharmaceutical container being carried by the second container transporter 24.

Although described in connection with an example computing system environment, embodiments of the aspects of the disclosure are operational with numerous other general purpose or special purpose computing system environments or configurations. The computing system environment is not intended to suggest any limitation as to the scope of use or functionality of any aspect of the disclosure. Moreover, the computing system environment should not be interpreted as having any dependency or requirement relating to any one or combination of components illustrated in the example operating environment. Examples of well-known computing systems, environments, and/or configurations that may be suitable for use with aspects of the disclosure include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the aspects of the disclosure may be described in the general context of data and/or processor-executable instructions, such as program modules, stored one or more tangible, non-transitory storage media and executed by one or more processors or other devices. Generally, program modules include, but are not limited to, routines, programs, objects, components, and data structures that perform particular tasks or implement particular abstract data types. Aspects of the disclosure may also be practiced in distributed computing environments where tasks are performed by remote processing devices that are linked through a communications network. In a distributed computing environment, program modules may be located in both local and remote storage media including memory storage devices.

In operation, processors, computers and/or servers may execute the processor-executable instructions (e.g., software, firmware, and/or hardware) such as those illustrated herein to implement aspects of the disclosure.

Embodiments of the aspects of the disclosure may be implemented with processor-executable instructions. The processor-executable instructions may be organized into one or more processor-executable components or modules on a tangible processor readable storage medium. Aspects of the disclosure may be implemented with any number and organization of such components or modules. For example, aspects of the disclosure are not limited to the specific processor-executable instructions or the specific components or modules illustrated in the figures and described herein. Other embodiments of the aspects of the disclosure may include different processor-executable instructions or components having more or less functionality than illustrated and described herein.

The order of execution or performance of the operations in embodiments of the aspects of the disclosure illustrated and described herein is not essential, unless otherwise specified. That is, the operations may be performed in any order, unless otherwise specified, and embodiments of the aspects of the disclosure may include additional or fewer operations than those disclosed herein. For example, it is contemplated that executing or performing a particular operation before, contemporaneously with, or after another operation is within the scope of aspects of the disclosure.

It is apparent that the elements, features, and/or teachings set forth in each embodiment disclosed herein are not limited to the specific embodiment(s) the elements, features and/or teachings are described in. Accordingly, it is understood that the elements, features and/or teachings described in one embodiment may be applied to one or more of the other embodiments disclosed herein, even if said elements, features and/or teachings where not described herein as being a part of said one or more of the other embodiments.

The Title, Field, and Background are provided to help the reader quickly ascertain the nature of the technical disclosure. They are submitted with the understanding that they will not be used to interpret or limit the scope or meaning of the claims. They are provided to introduce a selection of concepts in simplified form that are further described in the Detailed Description. The Title, Field, and Background are not intended to identify key features or essential features of the claimed subject matter, nor is it intended to be used as an aid in determining the claimed subject matter.

When introducing elements of aspects of the disclosure or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that several advantages of the aspects of the disclosure are achieved and other advantageous results attained.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively or in addition, a component may be implemented by several components.

The above description illustrates the aspects of the disclosure by way of example and not by way of limitation. This description enables one skilled in the art to make and use the aspects of the disclosure, and describes several embodiments, adaptations, variations, alternatives and uses of the aspects of the disclosure, including what is presently believed to be the best mode of carrying out the aspects of the disclosure. Additionally, it is to be understood that the aspects of the disclosure is not limited in its application to the details of construction and the arrangement of components set forth in the description or illustrated in the drawings. The aspects of the disclosure are capable of other embodiments and of being practiced or carried out in various ways. Also, it will be understood that the phraseology and terminology used herein is for the purpose of description and should not be regarded as limiting.

Having described aspects of the disclosure in detail, it will be apparent that modifications and variations are possible without departing from the scope of aspects of the disclosure as defined in the appended claims. It is contemplated that various changes could be made in the above constructions, products, and methods without departing from the scope of aspects of the disclosure. In the preceding specification, various embodiments have been described with reference to the accompanying drawings. It will, however, be evident that various modifications and changes may be made thereto, and additional embodiments may be implemented, without departing from the broader scope of the aspects of the disclosure as set forth in the claims that follow. The specification and drawings are accordingly to be regarded in an illustrative rather than restrictive sense.

What is claimed is:

1. A pharmaceutical container processor for processing pharmaceutical containers, the pharmaceutical container processor comprising:

a set of container operation stations along which a set of container operations occur, the set of container operation stations including:
 a storage station where pharmaceutical containers are stored;
 a first identification station where pharmaceutical containers are each identified after being removed from the storage station;
 a labeling station where a label is applied to pharmaceutical containers after pharmaceutical containers are identified at the first identification station;
 a second identification station where pharmaceutical containers are each identified after the label is applied to said pharmaceutical containers; and
 a outlet station where pharmaceutical containers are moved to after said pharmaceutical containers are identified at the second identification station; and
first and second container transporters configured to move each pharmaceutical container through the set of container operation stations, wherein each pharmaceutical container is transferred from the first container transporter to the second container transporter along the set of container operation stations.

2. The pharmaceutical container processor of claim 1, wherein the set of container operation stations further includes a transfer station where pharmaceutical containers are transferred from the first container transporter to the second container transporter.

3. The pharmaceutical container processor of claim 2, wherein the transfer between the first container transporter and the second container transporter at the transfer station is before the labeling station.

4. The pharmaceutical container processor of claim 2, further comprising a first holder at the transfer station, the first holder configured to hold a pharmaceutical container while said pharmaceutical container is transferred from the first container transporter to the second container transporter.

5. The pharmaceutical container processor of claim 4, wherein the first holder is proximate the first identification station such that the transfer station and first identification station are generally coincident.

6. The pharmaceutical container processor of claim 5, further comprising a second holder at the transfer station, the second holder configured to hold another pharmaceutical container while said another pharmaceutical container is transferred from the first container transporter to the second container transporter.

7. The pharmaceutical container processor of claim 6, wherein the second holder is proximate the first identification station.

8. The pharmaceutical container processor of claim 7, wherein the first and second holders are each configured to apply suction to said respective containers to hold said respective containers.

9. The pharmaceutical container processor of claim 8, further comprising a negative pressure source, wherein the negative pressure source is fluidly coupled to the first and second holders to apply the suction to hold said respective containers.

10. The pharmaceutical container processor of claim 9, wherein the first and second holders each includes a platform defining a plurality of inlets, the source of negative pressure fluidly coupled to the plurality of inlets to apply the suction to hold said respective container via the plurality of inlets.

11. The pharmaceutical container processor of claim 4, further comprising an identifier at the first identification station, the identifier configured to identify pharmaceutical containers using a label on each pharmaceutical container.

12. The pharmaceutical container processor of claim 11, wherein the first holder is configured to rotate the container while said container is held by the holder or the identifier is configured to rotate relative to the container as said container is held by the holder.

13. The pharmaceutical container processor of claim 1, wherein each pharmaceutical container is moved, in order, through the storage station, the first identification station, the labeling station, the second identification station and then the outlet station.

14. The pharmaceutical container processor of claim 1, wherein the first container transporter is configured to move pharmaceutical containers through a portion of the set of container operation stations and the second container transporter is configured to move pharmaceutical containers through another portion of the set of container operation stations generally simultaneously.

15. The pharmaceutical container processor of claim 1, further comprising:
   a repository at the storage station configured to store pharmaceutical containers;
   a first identifier at the first identification station configured to identify pharmaceutical containers;
   a labeler at the labeling station configured to apply the label to pharmaceutical containers; and
   a second identifier configured to identify pharmaceutical containers using the label applied by the labeler.

16. The pharmaceutical container processor of claim 1, further comprising a packager at the outlet station, the packager configured to package pharmaceutical containers in packages.

17. The pharmaceutical container processor of claim 16, further comprising a collector movable between a collection position and a clearance position, wherein in the collection position the collector is arranged to receive packages from the packager, and where in the clearance position the collector is arranged to not receive packages from the packager.

18. The pharmaceutical container processor of claim 17, further comprising a secondary collector arranged to receive packages from the packager when the collector is in the clearance position.

19. The pharmaceutical container processor of claim 17, wherein the collector comprises a conveyor.

20. The pharmaceutical container processor of claim 1, further comprising an enclosure defining a processing area, wherein the storage station, the first identification station, the labeling station, the second identification station, and the outlet station are at least partially disposed in the processing area.

* * * * *